US012632589B2

(12) United States Patent
Randhava et al.

(10) Patent No.: US 12,632,589 B2
(45) Date of Patent: May 19, 2026

(54) PRIVACY PRESERVING LOGGING

(71) Applicant: Apple Inc., Cupertino, CA (US)

(72) Inventors: Mohan S. Randhava, San Carlos, CA (US); Steven A. Myers, San Jose, CA (US); Jorge F. Pozas Trevino, San Mateo, CA (US); Pablo Antonio Gonzalez Cervantes, San Jose, CA (US); Yannick L. Sierra, San Francisco, CA (US)

(73) Assignee: Apple Inc., Cupertino, CA (US)

( * ) Notice: Subject to any disclaimer, the term of this patent is extended or adjusted under 35 U.S.C. 154(b) by 385 days.

(21) Appl. No.: 17/659,079

(22) Filed: Apr. 13, 2022

(65) Prior Publication Data
US 2022/0391534 A1    Dec. 8, 2022

Related U.S. Application Data

(60) Provisional application No. 63/197,469, filed on Jun. 6, 2021.

(51) Int. Cl.
*G06F 21/62* (2013.01)
*G16H 10/60* (2018.01)

(52) U.S. Cl.
CPC ......... *G06F 21/6245* (2013.01); *G16H 10/60* (2018.01)

(58) Field of Classification Search
CPC ....... G06F 21/6245; G16H 10/60; H04L 9/50; H04L 9/3265; H04L 2209/56
See application file for complete search history.

(56) References Cited

U.S. PATENT DOCUMENTS

| | | | |
|---|---|---|---|
| 10,032,039 B1 * | 7/2018 | Milman .............. | G06F 21/6209 |
| 2012/0239432 A1 * | 9/2012 | Desai .................... | G06Q 10/06 |
| | | | 705/3 |
| 2015/0161413 A1 * | 6/2015 | Calem ................ | G06F 21/6245 |
| | | | 705/51 |
| 2015/0213570 A1 * | 7/2015 | Li ......................... | H04L 9/3268 |
| | | | 705/51 |
| 2019/0103174 A1 * | 4/2019 | Power ................... | G06F 16/283 |
| 2019/0349426 A1 * | 11/2019 | Smith ................... | H04W 84/22 |
| 2019/0354693 A1 * | 11/2019 | Yoon ........................ | H04L 9/50 |
| 2020/0057867 A1 * | 2/2020 | Aunger ................. | H04L 63/0428 |
| 2020/0168306 A1 * | 5/2020 | Chen ..................... | G16H 10/60 |
| 2020/0327250 A1 * | 10/2020 | Wang .................... | G06N 20/00 |
| 2021/0271662 A1 * | 9/2021 | Muse .................... | G16H 50/70 |

* cited by examiner

*Primary Examiner* — Benjamin E Lanier
*Assistant Examiner* — Lydia L Noel
(74) *Attorney, Agent, or Firm* — Kilpatrick Townsend & Stockton LLP

(57)    ABSTRACT

A server system implemented by a service provider may store health data of a user according to a multi-node data structure. The server system may generate transaction records based on requests to access the health data. Responsive to requests for the transaction records, the server system may query a database that includes the health data and generate a data package based on the querying. The data package may be sent to a requesting system. The data package may be usable by the requesting system to identify which patient profiles were accessed by which physicians.

19 Claims, 22 Drawing Sheets

LOG RECORD 508

NODE INFORMATION 510
-MASTER RECORD DLID

ACCESS INFORMATION 512
-PHYSICIAN ID
-CURRENT TIME
-CURRENT IP ADDRESS
-OTHER ACCESS INFO.

LOG 128

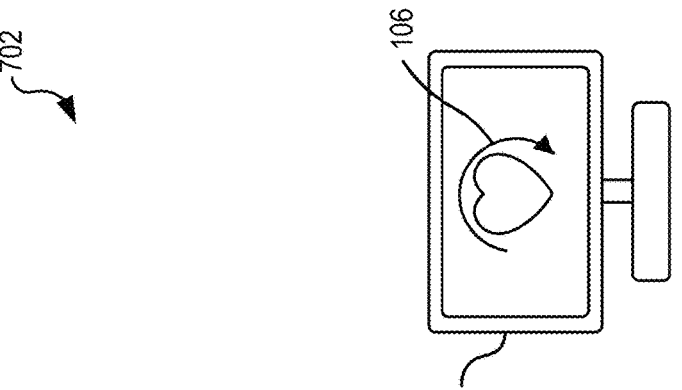
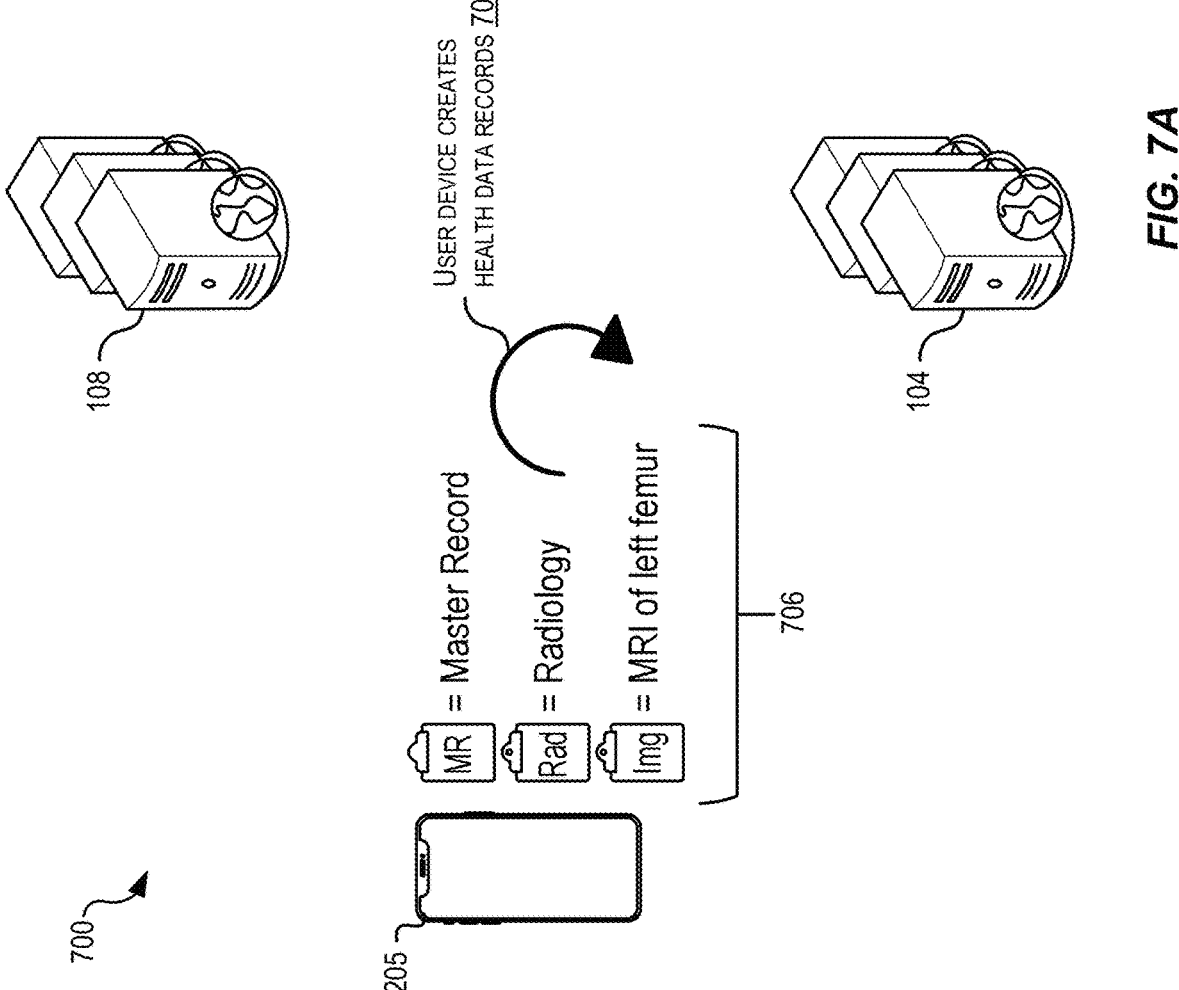
*FIG. 7A*

MR + $E_{PK_{DLID_1}}$(Patient ID, "Master Record"), $PK_{DLID_1}$

Rad + $E_{PK_{DLID_2}}$(Patient ID, "Radiology"), $PK_{DLID_2}$

Img + $E_{PK_{DLID_3}}$(Patient ID, "Jul 16, 2019, MRI of left femur"), $PK_{DLID_3}$

USER DEVICE CREATES
ENCRYPTED LOG DATA AND
ADDS TO HEALTH DATA
RECORDS 708

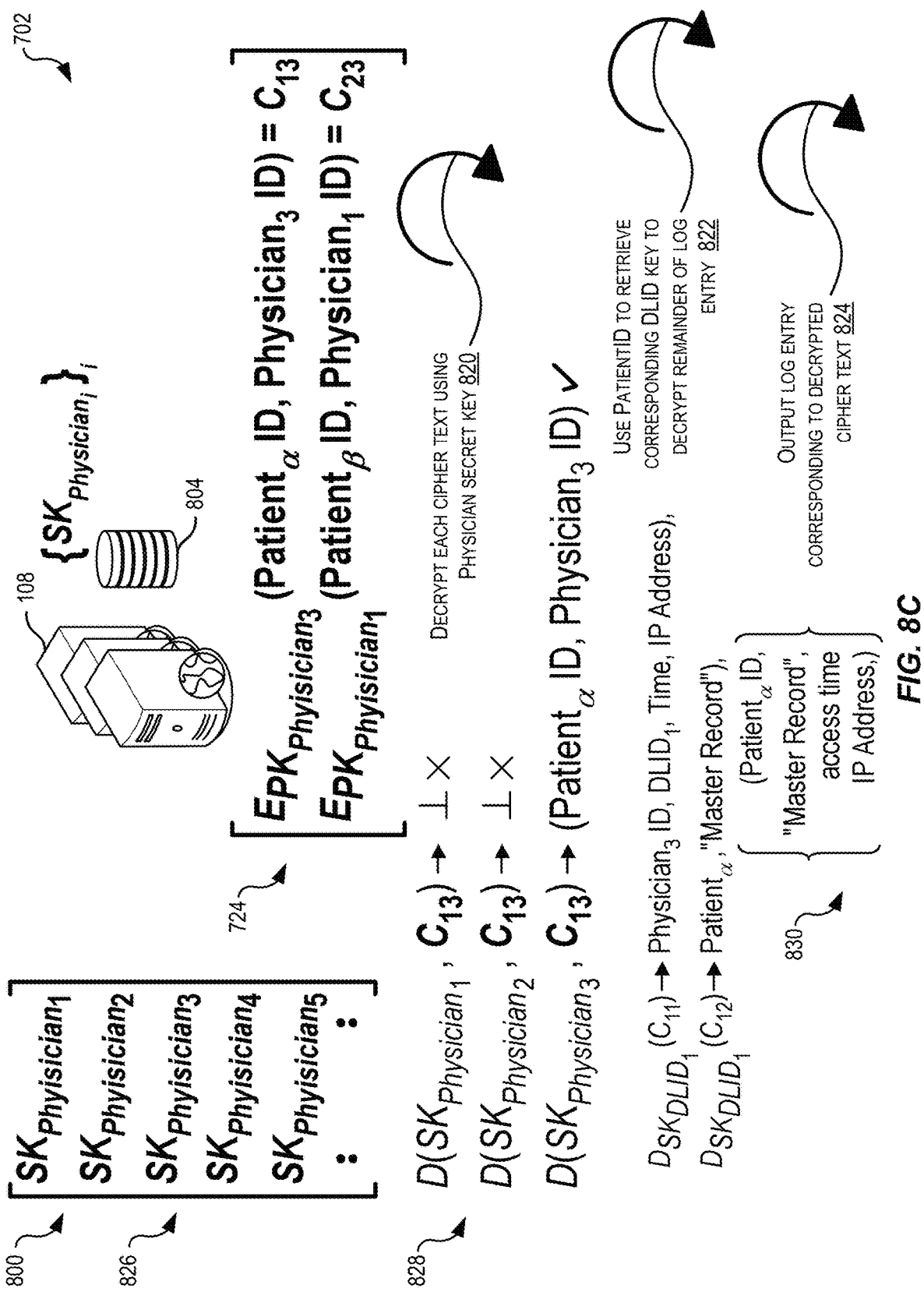

$$\begin{bmatrix} SK_{Phyisician_1} \\ SK_{Phyisician_2} \\ SK_{Phyisician_3} \\ SK_{Phyisician_4} \\ SK_{Phyisician_5} \\ \vdots \end{bmatrix}$$

$$\begin{bmatrix} E_{PK_{Phyisician_3}}(Patient_\alpha \text{ ID, Physician}_3 \text{ ID}) = C_{13} \\ E_{PK_{Phyisician_1}}(Patient_\beta \text{ ID, Physician}_1 \text{ ID}) = C_{23} \end{bmatrix}$$

$\{SK_{Physician_i}\}_i$ $D(SK_{Physician_1}, C_{13}) \rightarrow \perp \times$ $D(SK_{Physician_2}, C_{13}) \rightarrow \perp \times$ $D(SK_{Physician_3}, C_{13}) \rightarrow (Patient_\alpha \text{ ID, Physician}_3 \text{ ID}) \checkmark$

DECRYPT EACH CIPHER TEXT USING PHYSICIAN SECRET KEY 820

USE PATIENTID TO RETRIEVE CORRESPONDING DLID KEY TO DECRYPT REMAINDER OF LOG ENTRY 822

OUTPUT LOG ENTRY CORRESPONDING TO DECRYPTED CIPHER TEXT 824

$D_{SK_{DLID_1}}(C_{11}) \rightarrow$ Physician$_3$ ID, DLID$_1$, Time, IP Address), $D_{SK_{DLID_1}}(C_{12}) \rightarrow$ Patient$_\alpha$, "Master Record"), (Patient$_\alpha$ ID, "Master Record", access time IP Address,)

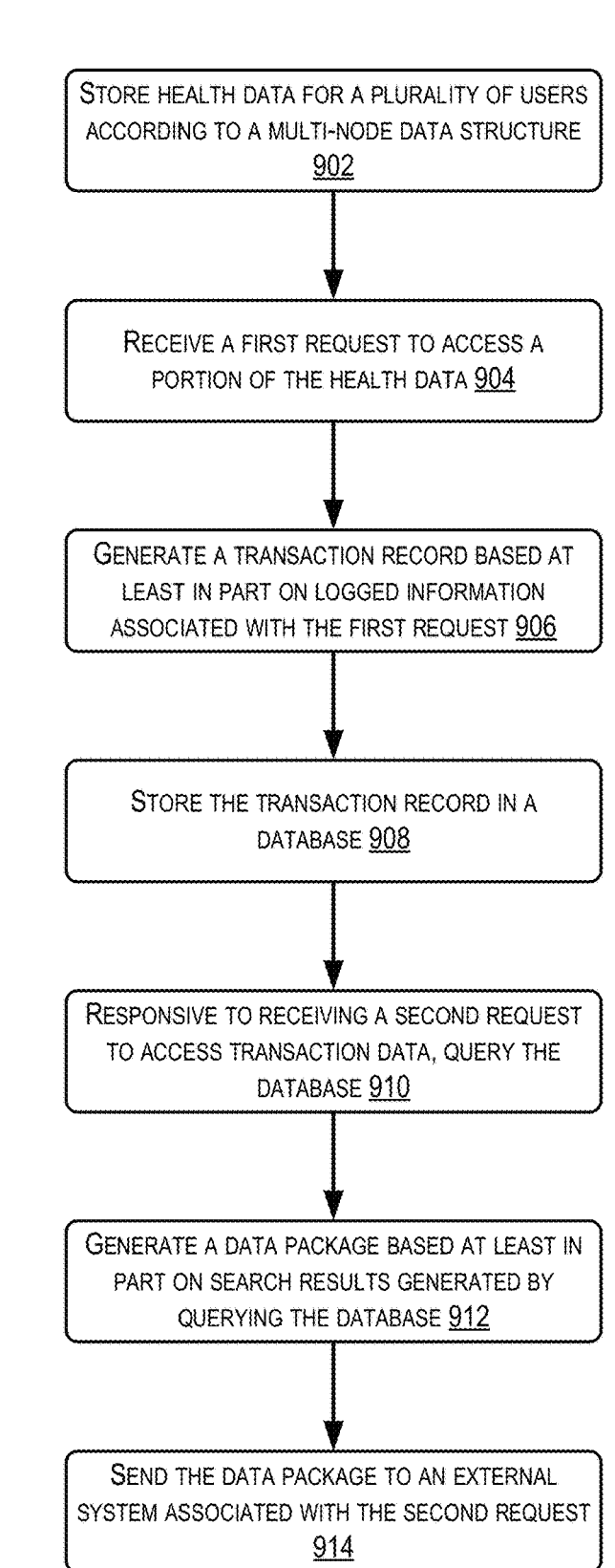

900

STORE HEALTH DATA FOR A PLURALITY OF USERS
ACCORDING TO A MULTI-NODE DATA STRUCTURE
902

RECEIVE A FIRST REQUEST TO ACCESS A
PORTION OF THE HEALTH DATA 904

GENERATE A TRANSACTION RECORD BASED AT
LEAST IN PART ON LOGGED INFORMATION
ASSOCIATED WITH THE FIRST REQUEST 906

STORE THE TRANSACTION RECORD IN A
DATABASE 908

RESPONSIVE TO RECEIVING A SECOND REQUEST
TO ACCESS TRANSACTION DATA, QUERY THE
DATABASE 910

GENERATE A DATA PACKAGE BASED AT LEAST IN
PART ON SEARCH RESULTS GENERATED BY
QUERYING THE DATABASE 912

SEND THE DATA PACKAGE TO AN EXTERNAL
SYSTEM ASSOCIATED WITH THE SECOND REQUEST
914

*FIG. 9*

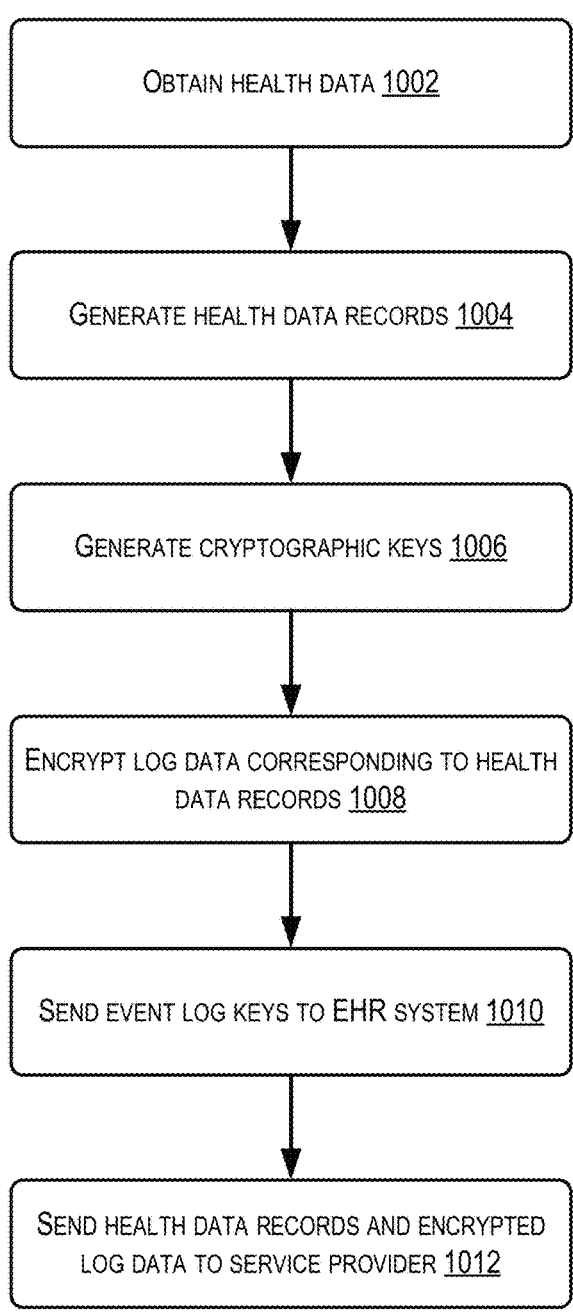

```
┌──────────────────────────────────────┐
│     OBTAIN HEALTH DATA 1002            │
└──────────────────────────────────────┘
                  │
                  ▼
┌──────────────────────────────────────┐
│  GENERATE HEALTH DATA RECORDS 1004     │
└──────────────────────────────────────┘
                  │
                  ▼
┌──────────────────────────────────────┐
│  GENERATE CRYPTOGRAPHIC KEYS 1006      │
└──────────────────────────────────────┘
                  │
                  ▼
┌──────────────────────────────────────┐
│  ENCRYPT LOG DATA CORRESPONDING TO     │
│  HEALTH DATA RECORDS 1008              │
└──────────────────────────────────────┘
                  │
                  ▼
┌──────────────────────────────────────┐
│  SEND EVENT LOG KEYS TO EHR SYSTEM 1010│
└──────────────────────────────────────┘
                  │
                  ▼
┌──────────────────────────────────────┐
│  SEND HEALTH DATA RECORDS AND ENCRYPTED│
│  LOG DATA TO SERVICE PROVIDER 1012     │
└──────────────────────────────────────┘
```

*FIG. 10*

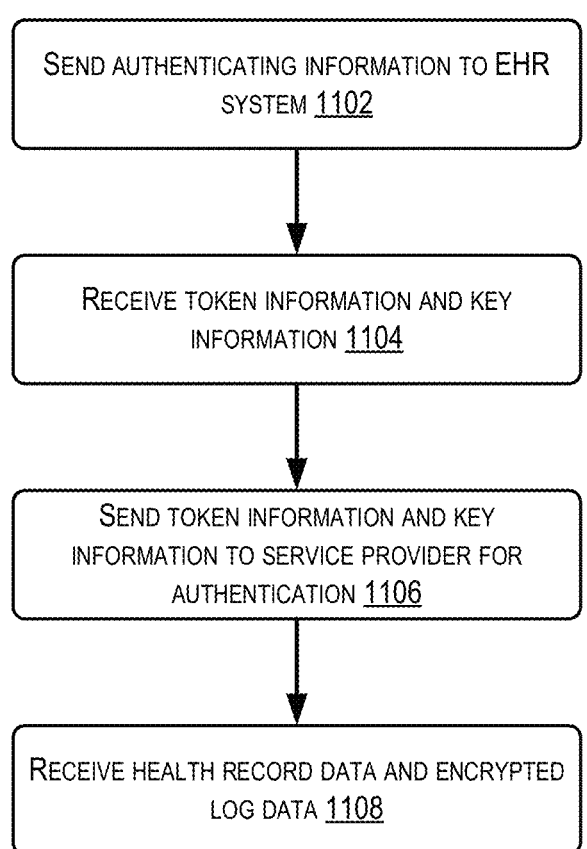
SEND AUTHENTICATING INFORMATION TO EHR SYSTEM 1102
RECEIVE TOKEN INFORMATION AND KEY INFORMATION 1104
SEND TOKEN INFORMATION AND KEY INFORMATION TO SERVICE PROVIDER FOR AUTHENTICATION 1106
RECEIVE HEALTH RECORD DATA AND ENCRYPTED LOG DATA 1108
*FIG. 11*

1200
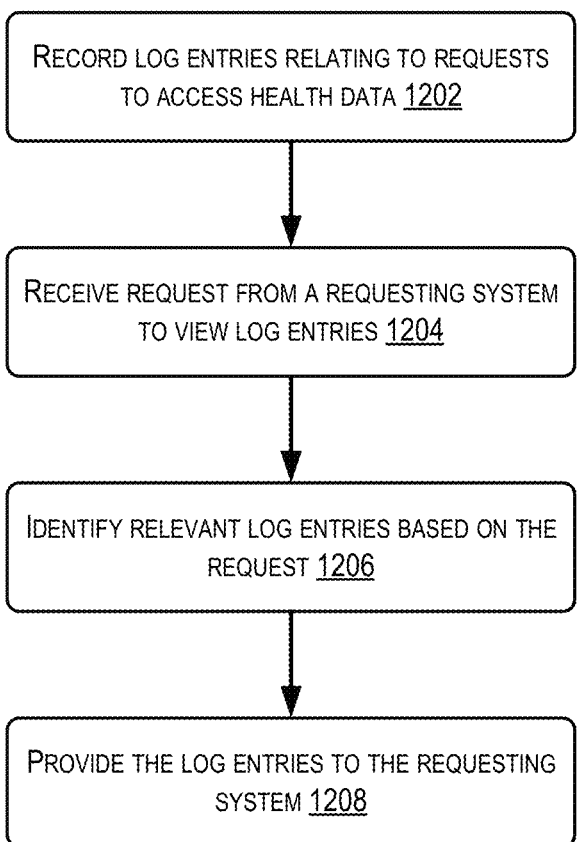
RECORD LOG ENTRIES RELATING TO REQUESTS TO ACCESS HEALTH DATA 1202
RECEIVE REQUEST FROM A REQUESTING SYSTEM TO VIEW LOG ENTRIES 1204
IDENTIFY RELEVANT LOG ENTRIES BASED ON THE REQUEST 1206
PROVIDE THE LOG ENTRIES TO THE REQUESTING SYSTEM 1208
*FIG. 12*

1300

BEGIN DECRYPTION OF LOG ENTRIES 1302

1304

LOG ENTRY INCLUDE THIRD CIPHER TEXT?

No

YES

TRY PHYSICIAN KEYS TO DECRYPT A FIRST PORTION OF LOG ENTRY 1314

TRY PATIENT KEYS TO DECRYPT LOG ENTRY 1306

USE PATIENT ID TO RETRIEVE CORRESPONDING PATIENT KEY 1316

USE PATIENT KEY TO DECRYPT REMAINING PORTIONS OF LOG ENTRY 1318

OUTPUT LOG RECORD 1308

1310

YES

OTHER LOG ENTRIES TO DECRYP?

No

END 1312

PRIVACY PRESERVING LOGGING

CROSS-REFERENCES TO RELATED APPLICATIONS

This application claims priority under 35 U.S.C. § 119(e) to U.S. Provisional Application No. 63/197,469, filed on Jun. 6, 2021 entitled, "PRIVACY PRESERVING LOG-GING," the contents of which are herein incorporated by reference.

BACKGROUND

Advancements have been made in recent years that allow users to download health data from remote electronic health record (EHR) systems to their mobile user devices. For example, a user may use their smartphone to connect to an endpoint of the EHR system and download a copy of their clinical health record. However, in some cases, such down-loads and other uploads from the smartphone may pass through a service provider or other third-party server, which could raise privacy concerns.

BRIEF SUMMARY

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes a com-puter-implemented method. The computer-implemented method includes storing, by a server system, health data for a plurality of users in accordance with a multi-node data structure, each node of the multi-node data structure being encrypted with a unique encryption key and being identified by a unique data identifier. The computer-implemented method also includes receiving, by the server system and from a clinician dashboard associated with a health institu-tion, a first request to access a portion of the health data, the first request including (i) a particular unique data identifier associated with a particular node of the multi-node data structure, and (ii) a user identifier associated with a health care professional of the health institution. The computer-implemented method also includes generating, by a server system, a transaction record based at least in part on logged information associated with the first request, the transaction record identifying (i) the particular unique data identifier, (ii) the user identifier associated with the user of the health institution, and (iii) metadata associated with the first request. The computer-implemented method also includes responsive to receiving a second request to access transac-tion data corresponding to the health data, querying, by the server system, a database accessibly by the server system in accordance with a search parameter included in the second request. The computer-implemented method also includes generating, by the server system, a data package based at least in part on search results generated by querying the database, the data package including the transaction record. The computer-implemented method also includes sending, by the server system, the data package to an external system associated with the second request, the transaction record being configured to enable the external system to identify a patient profile associated the particular unique data identifier and the user identifier associated with the health care pro-fessional. Other embodiments of this aspect include corre-sponding computer systems, apparatus, and computer pro-grams recorded on one or more computer storage devices, each configured to perform the actions of the methods.

One general aspect includes a computer-implemented method. The computer-implemented method includes receiving a cryptographic key and a unique data identifier from an electronic health record (EHR) system. The com-puter-implemented method also includes sending, to a ser-vice provider, a first request for health data associated with a user, the first request including a unique data identifier that identifies an encrypted data node of a multi-node data structure used by the service provider to store the health data. The computer-implemented method also includes receiving, from the service provider, node information rep-resentative of the encrypted data node. The computer-implemented method also includes receiving, from the ser-vice provider, access information corresponding to the request and the node information. The computer-imple-mented method also includes generating a transaction record based at least in part on the node information and the accessing information, the transaction record identifying (i) the unique data identifier, (ii) user identifier associated with a user of a health institution who requested the health data, and (iii) metadata associated with the first request. The computer-implemented method also includes comparing the transaction record with a mapping including user identifiers and patient identifiers. The computer-implemented method also includes identifying a set of records of a particular patient accessed by the user based at least in part on the comparing. Other embodiments of this aspect include cor-responding computer systems, apparatus, and computer pro-grams recorded on one or more computer storage devices, each configured to perform the actions of the methods.

One general aspect includes a computer-implemented method. The computer-implemented method includes obtaining health data from at least one of (i) a first sensor of a mobile device, (ii) a second sensor of a wearable device, or (iii) a first electronic health record (EHR) system. The computer-implemented method also includes generating health data records based at least in part on the obtained health data, the health data records organized and stored on the mobile device according to a multi-node data structure, each node of the multi-node data structure identifiable by a unique data identifier. The computer-implemented method also includes generating a first set of cryptographic keys corresponding to one or more nodes of the multi-node data structure at which the health data records are stored. The computer-implemented method also includes encrypting log data corresponding to the health data records. The computer-implemented method also includes associating the encrypted log data with the health data records. The computer-imple-mented method also includes sending the associated encrypted log data and the health data records to a service provider for storage. The computer-implemented method also includes sending a second set of cryptographic keys to the first EHR system or to a second EHR system, the second set of cryptographic keys configured to decrypt the log data. Other embodiments of this aspect include corresponding computer systems, apparatus, and computer programs recorded on one or more computer storage devices, each configured to perform the actions of the methods.

One general aspect includes a computer-implemented method. The computer-implemented method also includes beginning decryption of a set of encrypted log entries corresponding to access events of health data. The computer-implemented method also includes determining whether a log entry of the set of encrypted log entries includes a portion including a third ciphertext corresponding to a set of encrypted user identifiers. The computer-implemented method also includes in the event log entry includes the third cipertext: trying a set of first cryptographic keys to decrypt the third ciphertext of the log entry, the set of first cryptographic keys associated with to one or more physicians; upon successful decryption of the third ciphertext, retrieving a patient identifier previously encrypted as the third ciphertext; using the patient identifier to retrieve a second cryptographic key associated with a patient; and using the second cryptographic key to decrypt one or more other portions of the log entry. Other embodiments of this aspect include corresponding computer systems, apparatus, and computer programs recorded on one or more computer storage devices, each configured to perform the actions of the methods.

BRIEF DESCRIPTION OF THE DRAWINGS

FIG. 7A-7G illustrate a block diagram showing an example system and an example process for logging transaction data and encrypting and decrypting information about logged transactions in connection with requests for such information, according to at least one example.

FIGS. 8A-8C illustrate a block diagram showing the system of FIG. 7 and an example process for sharing and decrypting logged transaction data associated with accessing health data, according to at least one example.

FIG. 9 illustrates a flow chart showing an example process for generating and sharing transaction data relating to a health data, according to at least one example.

FIG. 10 illustrates a flow chart showing an example process for generating and sharing transaction data relating to a health data, according to at least one example.

FIG. 11 illustrates a flow chart showing an example process for authenticating a physician user of a first system to access health data from a second system, according to at least one example.

FIG. 12 illustrates a flow chart showing an example process for generating log entries based on requests and sharing log entry information based on requests, according to at least one example.

4

Figure 13:
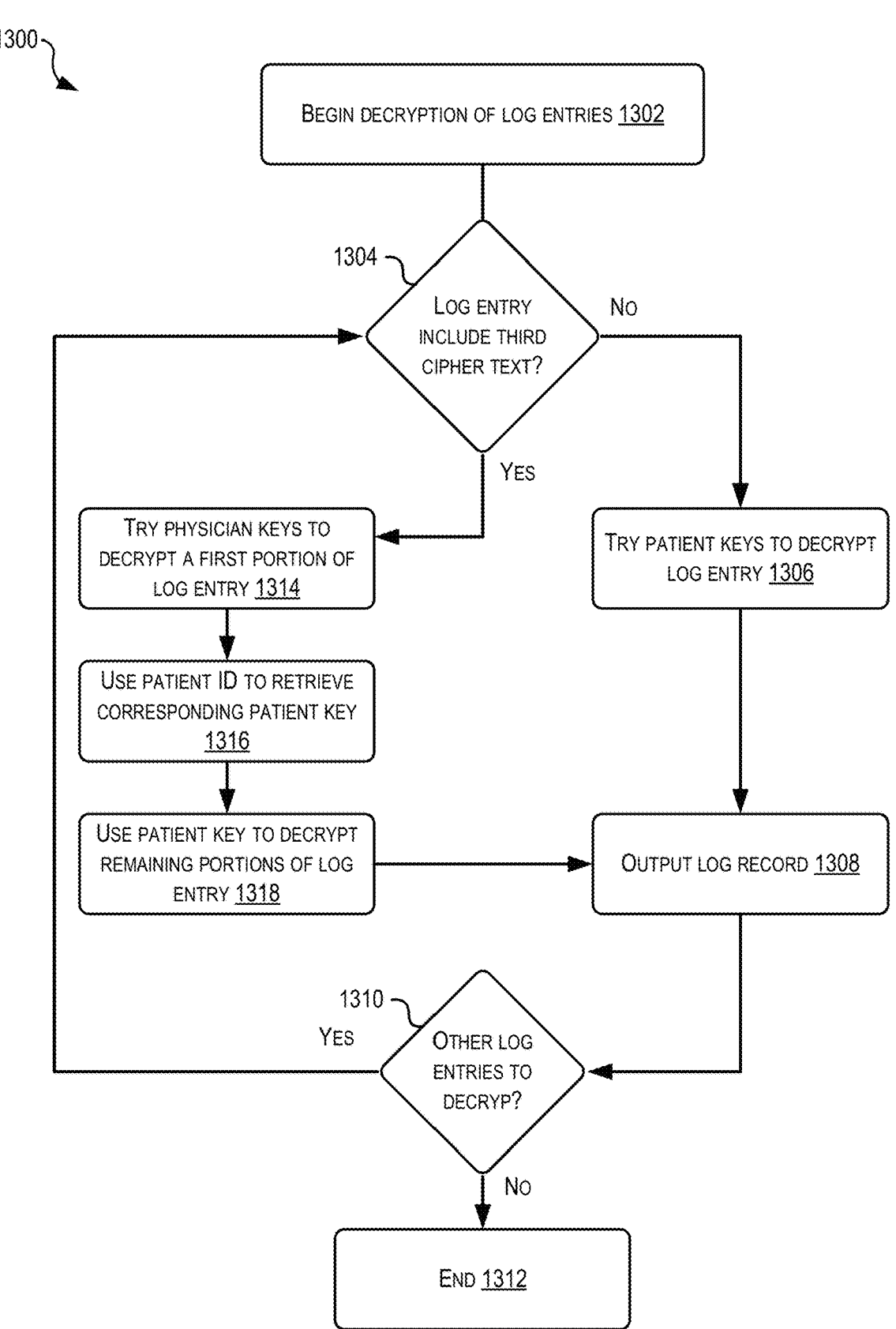

FIG. 13 illustrates a flow chart showing an example process for decrypting log entries, according to at least one example.

Figure 14:
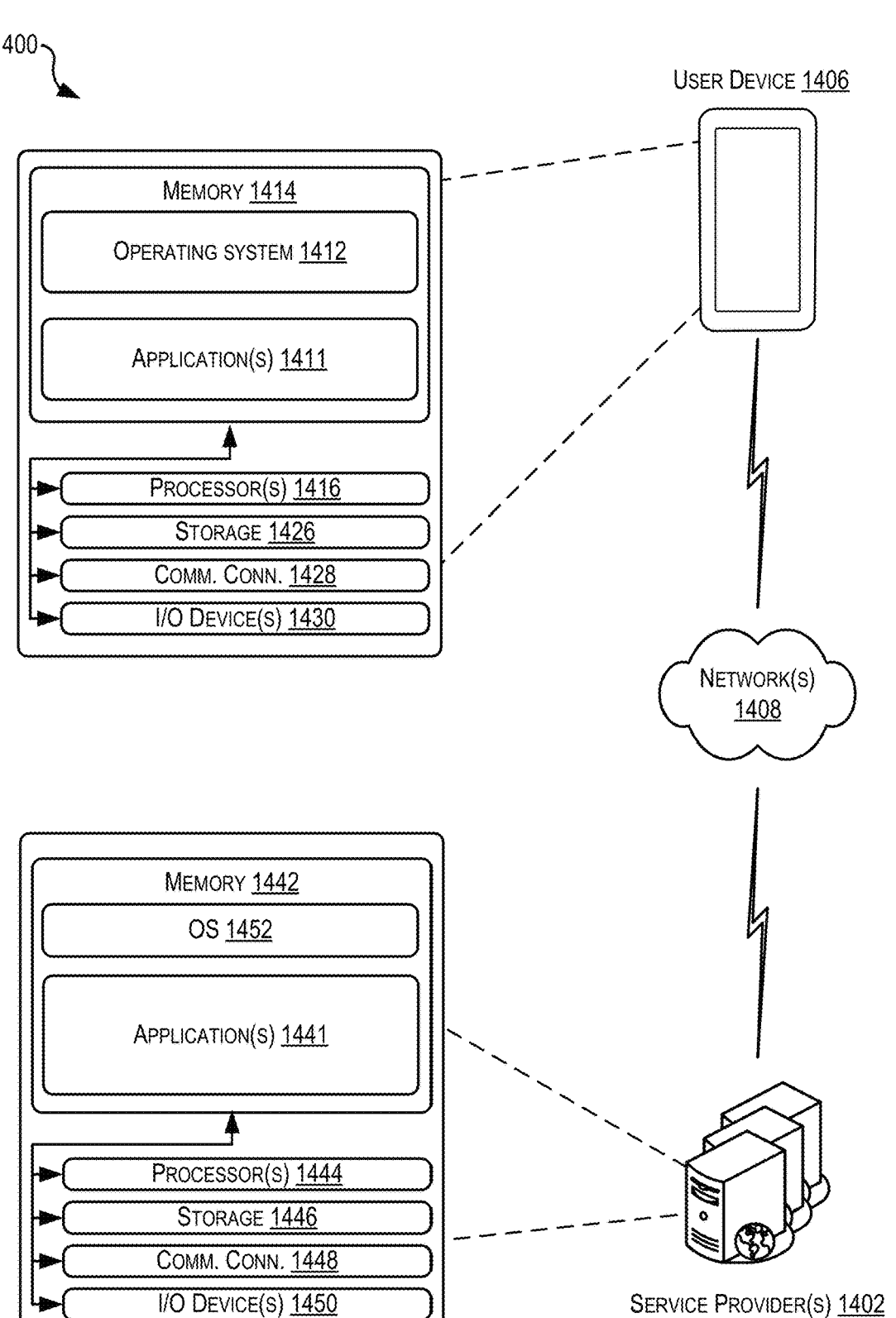

FIG. 14 illustrates an example architecture or environment configured to implement techniques described herein, according to at least one example.

DETAILED DESCRIPTION

In the following description, various examples will be described. For purposes of explanation, specific configurations and details are set forth in order to provide a thorough understanding of the examples. However, it will also be apparent to one skilled in the art that the examples may be practiced without the specific details. Furthermore, well-known features may be omitted or simplified in order not to obscure the example being described.

Examples of the present disclosure are directed to, among other things, methods, systems, devices, and computer-readable media that securely logs transaction data of users (e.g., health care providers) who access sensitive health data of patients securely stored by a service provider. The service provider may be part of a health data storage platform that enables users to share health data with their health care providers. This health data may have been downloaded from a different health care provider, logged by the users' respective user devices (e.g., smartphone, watch, or other wearable or non-wearable user device), and/or obtained in any other suitable manner. The logging is performed by the service provider in a manner that enables a high degree of privacy, ensuring that identities of the requesting health care provider and the subject patient are kept hidden from the service provider. The logged transactional data may be particularly useful for the health care provider for auditing the use of health data storage platform, responding to security incidents, and the like. Thus, after logging has been performed, the service provider may respond to requests for transaction data by querying a database in which the transaction data is stored. The queries may be targeted using at least some of the same data fields logged by the service provider. Such queries may be vague with respect to the database because much of the information stored by the database will be encrypted. The service provider may provide the retrieved information with the health care provider, and the health care provider may decrypt and filter the data that is irrelevant to its request.

While the techniques are described with respect to medical and health data, the techniques are not limited to this type of data. In particular, the system can be used for any suitable arbitrary record that may have needs for maintaining privacy.

To maintain data security, the health data storage platform ensures patient privacy by minimizing the types of users and/or systems that have access to patient health data and logs data in a manner that builds upon the existing privacy features of the platform. While no single element alone within the platform is perfectly suited for logging transaction data, the techniques described herein strike a balance between maintaining ultimate patient privacy and logging sufficient transaction data to be actionable when needed (e.g., to respond to security incidents). One way in which patient privacy is protected is that the logging data in the abstract is de-identified. Alone when combined with other datasets available only to the operator of the EHR system can it be identified which provider profiles were used to access which patient records and when.

As described in detail herein, according to the health data sharing platform, an existing electronic health record (EHR) system is used to authenticate health care providers who use a custom-built application (e.g., clinician dashboard) operated within the EHR system to view sensitive health data. The EHR system may be capable of tracking which patient files are requested for viewing from the service provider, but may not track which particular files within the patient files are accessed. The clinician dashboard may track which particular files are requested, but may not include storage to store transaction data and could be bypassed by a malicious user to request patient files surreptitiously. The service provider may track which particular files are served to the clinician dashboard, but may be incapable of tracking anything about the files (they are encrypted) or who the files belong to (they are private with respect to the service provider). The techniques described herein rely on the service provider for primary logging of the transaction data, which, in some examples, may be encrypted and/or combined in other non-conventional ways to generate a dataset that ensures higher degrees of privacy. For example, the service provider may log specific information about what records are accessed and the clinician dashboard may share accessing information (e.g., patient identifier, physician identifier, current time, current IP address) with the service provider. The service provider may combine these two types of information and create a log record that is shared with the EHR system. In this example, the EHR system may store the log record in a log accessible by the EHR system and/or a requesting system.

In a different example, a user device may store health data in connection with encrypted log data associated with access events. The user device may then share event log keys corresponding to the access events with the EHR system, and share the stored health data and encrypted log data with the service provider. The clinician dashboard may then be authenticated by the EHR system using a patient identifier and a physician identifier. In response, the clinician dashboard may receive key information, which may be encrypted. The key information may include, in some examples, a set of lookup information, a decryption key, a verification key, and a DLID (e.g., an address of the master record). In some examples, the key information may include an encrypted physician identifier. The clinician dashboard may provide the key information and the physician identifier to the service provider. Since the key information (e.g., the DLID) specifically maps to a record of the patient, the service provider is able to return the health data stored at the address identified by the DLID. In this manner, the service provider will be unable to identify the patient with whom the health data is associated, but is able to log the physician identifier that made the request. In some examples, the clinician dashboard also provides the encrypted information, which may include the physician identifier and the patient identifier. In some examples, the clinician dashboard may share a public key, which may be used by the service provider to encrypted the physician identifier. In some examples, the clinician dashboard may send an encrypted physician identifier directly to the service provider. This encrypted information may be associated with the transaction for the records received by the service provider. At this point, the service provider may generate a log of the transaction that includes information identifying an encrypted specific node identifier (e.g., the files accessed), an encrypted physician identifier (e.g., the physician that accessed the files), and other related information such as a time and an IP address of the access. The ciphertext for the specific node identifier may then be randomized with respect to the patient identifier and the health data from the node. When the logs need to be produced, the event log keys may be used to decrypt the transaction data.

The examples described herein address a number of technical problems and provide for a number of technical improvements. In some examples, these improvements additionally improve the functioning of various components of a system in which the techniques are implemented. For example, the techniques and system architecture described herein improve systems that privately maintain certain aspects of patient health data. The service provider has the ability to track all accesses of patients' data from particular health institutions while preserving the patients' anonymity with respect to the service provider. Thus, the service provider is able to build access logs that track who accessed the patients' data but in a way that the service provider cannot view associations between the logs, the patients, and the data. Thus, the logging can be done in a privacy-preserving manner. The service provider is the only entity that can attest to which records were accessed as part of the building the access logs, but, given the unique arrangement of cryptographic information, the service provider cannot access these logs. Rather, the health institutions are the sole entities that can access the logs and reconstruct who accessed what information and when. Thus, the analysis of these access logs may be performed in a manner that is viable and meaningful to the health institutions, because the access logs can only be returned upon their demand and to no one else, given that only the health institutions have been granted the cryptographic information to extract knowledge from these logs. Thus, the techniques described herein provide for private and confidential access logging that is uniquely performed per health institution.

In some examples, the techniques described herein may also improve the functioning of the electronic user devices on which certain techniques are implemented by reducing the number of click-throughs, user interface views, buttons, and the like that must be accessed for performing certain operations. This may enable the user device to operate more efficiently than prior approaches.

Figure 1:
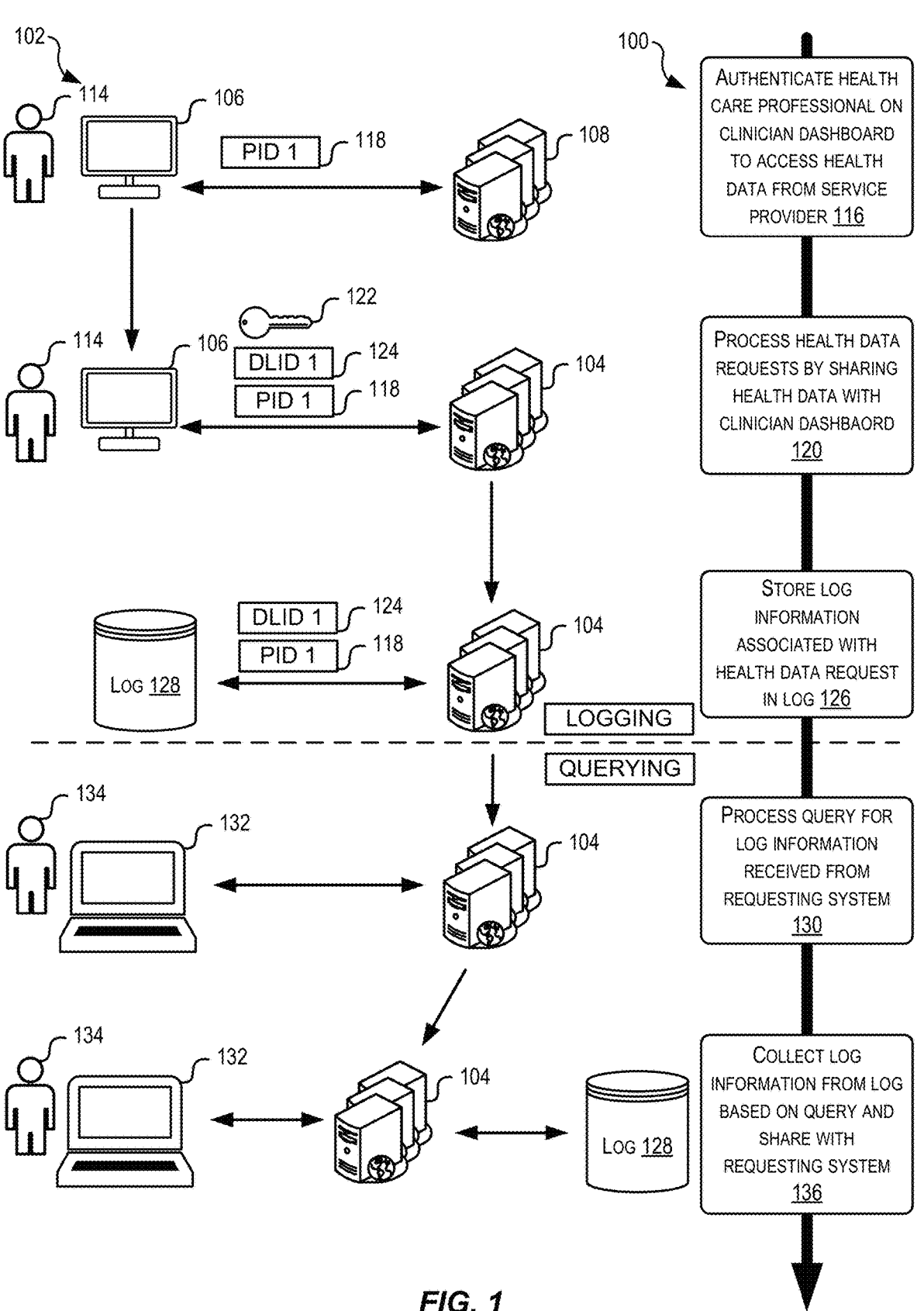
FIG. 1 illustrates a block diagram and a flowchart showing an example process for generating and sharing transaction logs relating to electronic health records, according to at least one example.

Turning now to the figures, FIG. 1 illustrates a block diagram 102 and a flowchart showing a process 100 for generating and sharing transaction logs relating to electronic health records, according to at least one example. The portion of the flowchart above the horizontal dashed line generally relates to logging transaction data and the portion below the horizontal dashed line generally relates to querying the transaction data.

The diagram 102 includes a service provider 104, which is any suitable combination of computing devices such as one or more server computers, which may include virtual resources, capable of performing the functions described with respect to the service provider 104. For example, the service provider 104 may include one or more different servers and/or services dedicated to handling different aspects of sharing health data, collecting transaction logs relating to accessing health data by a clinician dashboard 106, and providing information associated with transaction logs, when appropriate, to requesting systems 132.

The diagram 102 also includes an electronic health record (EHR) system 108. The EHR system 108 is associated with at least one health institution and used to manage electronic health record data from the institution. In some examples, a single EHR system 108 is associated with multiple health institutions and used to manage electronic health record data from the multiple institutions. In particular, the EHR system 108 may store, organize, and/or otherwise manage health record data generated by medical professionals of the health institutions. The EHR system 108 may include one or more gateways, each including one or more endpoints to enable multiple connections between the EHR system 108 and other electronic devices. In some examples, user devices, such as smartphones and tablets, may interact with the EHR system 108 using any suitable interfaces such as gateway application programming interfaces (API) or via patient portals including graphical user interfaces. The gateway APIs may define a set of function calls for communications between the EHR system 108 and the user device.

The EHR system 108 may also provide one or more applications such as the clinician dashboard 106 to enable health care professionals 114 to view health data stored by the service provider 104 and/or the EHR system 108. The clinician dashboard 106 may be any application accessible on any suitable electronic user device capable of communicating with other electronic devices over a network such as the Internet, a cellular network, or any other suitable network.

FIGS. 1 and 9-13 illustrate example flow diagrams showing processes 100, 900, 1000, 1100, 1200, and 1300, according to at least a few examples. These processes, and any other processes described herein, are illustrated as logical flow diagrams, each operation of which represents a sequence of operations that can be implemented in hardware, computer instructions, or a combination thereof. In the context of computer instructions, the operations may represent computer-executable instructions stored on one or more non-transitory computer-readable storage media that, when executed by one or more processors, perform the recited operations. Generally, computer-executable instructions include routines, programs, objects, components, data structures, and the like that perform particular functions or implement particular data types. The order in which operations are described is not intended to be construed as a limitation, and any number of the described operations can be combined in any order and/or in parallel to implement the processes.

Additionally, some, any, or all of the processes described herein may be performed under the control of one or more computer systems configured with specific executable instructions and may be implemented as code (e.g., executable instructions, one or more computer programs, or one or more applications) executing collectively on one or more processors, by hardware, or combinations thereof. As noted above, the code may be stored on a non-transitory computer-readable storage medium, for example, in the form of a computer program including a plurality of instructions executable by one or more processors.

The process 100 begins at block 116 by the EHR system 108 authenticating a health care professional (e.g., 114) on clinician dashboard (e.g., the clinician dashboard 106) to access health data from service provider (e.g., the service provider 104). This may include the health care professional 114 using the clinician dashboard 106 to provide a provider identifier 118 (PID 1) to the EHR system 108. In some examples, the authentication may be part of a decentralized authentication protocol such as OpenID to authenticate the clinician dashboard 106.

At block 120, the process 100 includes processing health data requests by sharing health data with the clinician dashboard 106. For example, after the clinician dashboard 106 has been authenticated, the EHR system 108 may enable the clinician dashboard 106 to begin interacting with the service provider 104 to access health data stored by the service provider 104. For example, the health data may be stored according to the multi-node data storage structure, as described in more detail with respect to FIG. 4. In some examples, each node of the storage structure may be encrypted and be identified by a corresponding unique data identifier. Thus, processing the health data requests may include receiving from the clinician dashboard 106, key information 122, the data node identifier 124 (referred to herein as a document lookup identifier (DLID) 1 or a Unique Data Identifier (UID)), and the provider identifier 118. With this information, the service provider 104 may use the data node identifier 124 to identify the root node at which the health data is stored by the service provider 104 and use the key information 122 to decrypt the health data stored at the node and provide the same to the clinician dashboard 106.

At block 126, the process 100 includes storing log information associated with the health data requests (from block 120) in log (e.g., log 128). For example, after the service provider 104 has processed the health data requests at block 120, the service provider 104 may store the data node identifier 124 and the provider identifier 118 in the log 128. In some examples, the log information may be encrypted in the log 128. The log 128 may be any suitable database or other data storage structure configured to store the log information. In some examples, metadata associated with the health data requests may also be stored in connection with the provider identifier 118 and the data node identifier 124. Such metadata may include, for example, a time associated with the request, an IP address associated with the request, and any other suitable information associated with the request.

At block 130, the process 100 includes processing a query for log information received from a requesting system. For example, the service provider 104 may receive a query from the requesting system 132 operated by a requesting user 134. The requesting system 132 may be any suitable user device, system, or the like usable for requesting the log information. In some examples, the requesting user 134 may be associated with the requesting system 132. In some examples, the requesting user 134 may query the log information responsive to a data breach or other security incident. For example, if health care professional credentials were compromised, the requesting user 134 may use the requesting system 132 to query the log 128 to determine whether the compromised credentials had been used to access patient data.

At block 136, the process 100 includes collecting log information from log based on the query and sharing the same with requesting system. For example, the service provider 104 may collect the log information from the log 128 using the query received at block 130. Once the service provider 104 has collected the log information, the service provider 104 may share the collected information with the requesting system 132. For example, the log information may be usable by the requesting system 132 to determine which health care professional profiles were used to access which patient profiles and when. In some examples, the query received at 130 may identify the provider identifier 118 and/or any other information stored within the log 128. Thus, the information from the log 128 may be used by the requesting system 132 alone and/or combined with other dataset(s) to identify which health care professional profiles were used to access which patient profiles and when.

Figure 2:
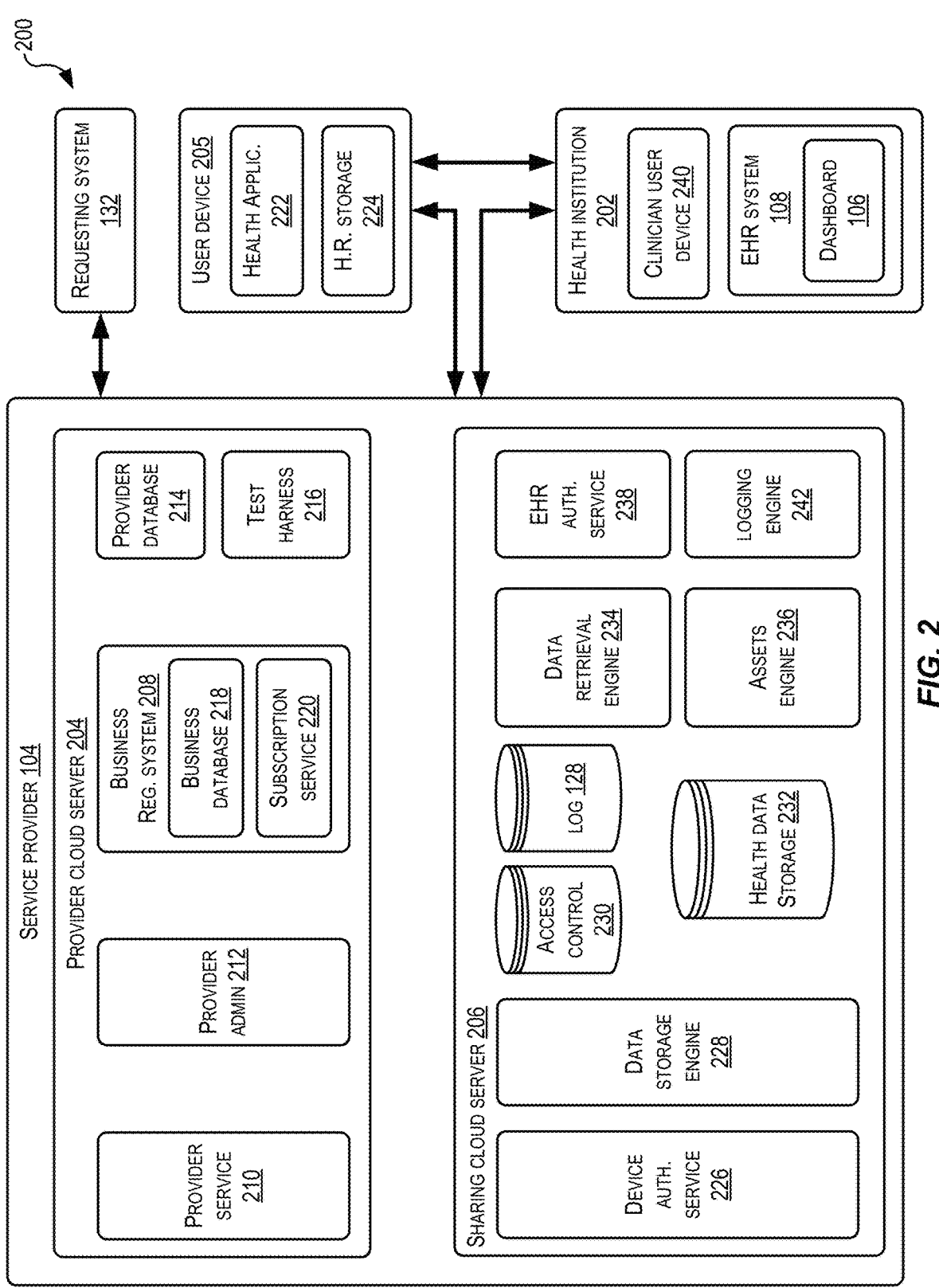
FIG. 2 illustrates a block diagram showing an example architecture or system for generating and sharing transaction logs relating to electronic health records, according to at least one example.

FIG. 2 illustrates a block diagram showing an example architecture or system 200 for enabling sharing of health data from user devices with electronic health record systems, according to at least one example. The system 200 includes a few elements introduced in FIG. 1. In particular, the system 200 includes the service provider 104, the EHR system 108 (e.g., one or any other suitable number of EHR systems) associated with a health institution 202, the dashboard 106 (e.g., one or more other suitable clinician dashboards), and the requesting system 132. As appropriate and as illustrated by the arrows, the elements of the system 200 may be communicatively coupled via one or more suitable communication networks. For example, the service provider 104, a user device 205, and the EHR system 108 may be configured to communicate with each other via one or more networks, as described herein and is known in the art. In some examples, the requesting system 132 may be in network communication with the service provider 104 and/or the health institution 202. The requesting system 132 may be operated by a third-party entity (e.g., an entity that is different from the ones that operate the service provider 104, the user device 205, and the health institution 202). In some examples, however, the requesting system 132 may be associated with, hired by, or otherwise controlled by the same entity that operates the health institution 202. For example, in the event of a security incident, the health institution 202 may request transaction information about a set of transactions during a period of interest. The service provider 104 may provide a portal, API resources, or some other data access point that requesting system 132 can use to request transaction data. In this example, the health institution 202 may use the service provider 104's data access point to request the information.

Beginning with the service provider 104, the service provider 104 includes a provider cloud server 204 and a sharing cloud server 206. Generally, the provider cloud server 204 includes one or more server computers, which may be virtual, and is configured to onboard health institutions to enable sharing of health data, manage registrations of the health institutions once onboarded, and conduct tests of endpoints of the EHR systems 108 of the health institutions 202 to ensure correct operation with the sharing system provided by the service provider 104. Generally, the sharing cloud server 206 includes one or more server computers, which may be virtual, and is configured to manage sharing of health data by user devices 205 with the service provider 104 and the health institution 202. In particular, different elements of the sharing cloud server 206 manage different aspects of sharing including authorization of user devices 205 and EHR systems 108, data retrieval, and the like.

The provider cloud server 204 includes a business registration system 208, a provider service 210, a provider admin 212, a provider database 214, and a test harness 216. Business registration system 208 may be any suitable collection of hardware and software components configured to collect, store, update, and otherwise manage business locations including those of the health institutions 202. For example, the business registration system 208 may include a business database 218 and a subscription service 220 to enable subscription of the EHR systems 108 of the health institutions 202. When a health institution 202 is subscribed and active, the user devices 205 may be allowed to share health data with the EHR system 108 and connect to and download health record data from the EHR system 108 (e.g., a gateway of the EHR system 108).

As part of subscribing and managing subscriptions, the subscription service 220 may include functionality to collect, store, update, and otherwise manage business locations. In some examples, the subscription service 220 provides one or more user interfaces by which authorized users of the health institution 202 may input information about their location. This information may include geographic information (e.g., a physical address and pin on a map), image information (e.g., logos), contact information (e.g., business, legal, technical), and any other information relating to a business. The subscription service 220 may also be configured to create and/or update record entries in the business database 218 based on information received. For example, an authorized user associated with the health institution 202 may share business information with the subscription service 220. Once this information has been shared and validated, the business information may published for public consumption (e.g., indexed for searching, made available on a map platform, shared directly with users).

The business database 218 may maintain the collected business information and any relationships between entities represented by the business information. In some examples, the business registration system 208 may be used to register other business entities (not just health institutions 202). Records for the health institutions 202 may be maintained in both the business database 218 and a provider database 214 maintained by the provider cloud server system 204. In some examples, the business registration system 208 shares business information with the provider sharing cloud server 206 in any suitable manner.

Turning now to the provider service 210, generally, the provider service 210 may validate the EHR systems 108, maintain information about the health institutions 202 and associated EHR systems 108, enable searching of the health institutions 202 associated with the EHR systems 108, and manage access of the user devices 205 to the EHR systems 108. The provider cloud server 204 may be implemented in the "cloud." The provider service 210 may also maintain information about the health institutions 202 and associated EHR systems 108 in the provider database 214, enable searching of the health institutions 202 associated with the EHR systems 108, and manage access of the user devices 205 to the EHR systems 108. In some examples, the user device 205 sends requests to search for the health institutions 202 to the provider service 210. The provider service 210 processes these requests and returns results. In some examples, as part of establishing a connection with one of the EHR systems 108, the user device 205 will check in with the provider service 210 to determine whether any configuration information associated with the EHR system 108 has changed. The configuration information, which may be stored in the provider database 214, may include API information, provider identifiers, status indicator information, and any other suitable information relating to the configuration of the EHR system 108 and/or other entities associated with the EHR system 108.

As part of subscribing a health institution 202, the test harness 216 may be used to test and/or otherwise validate that a test user using a test user device 205 can connect to and download data from the EHR system 108. In this manner, the test harness 216 may simulate actions that one of the user devices 205 may perform to connect to the EHR system 108. In some examples, the test harness 216 may test this connection when a health institution 202 is first subscribed and at other times after the initial subscription. For example, the connection may be tested periodically when certain conditions are fulfilled and under any other circumstance. If the test is positive, a status indicator(s) in the provider database 214 associated with the health institution 202, the EHR system 108, and/or a gateway associated with the EHR system 108 may be updated to reflect that the EHR system 108 or the gateway is/are active. If the test is negative, the status indicator(s) may be updated to reflect that the EHR system 108 is inactive. When active, the user devices 205 may be capable of connecting to the gateways of the EHR systems 108. When inactive, the user devices 205 may be unable to connect to the gateways of the EHR systems 108.

The provider admin 212 may generally be used by an administrator or other authorized user to manage aspects of the provider cloud server 204.

The user device 205 may include a health application 222 and a health record storage 224. Generally, the user devices 205 may be associated with and operated by different users (e.g., patients of the health institutions 202). Functionally, the health application 222 may enable the user devices 205 to communicate with the provider cloud server 204 (e.g., to search for the health institutions 202, obtain configuration information about the health institutions 202, and perform other techniques), communicate with the EHR systems 108 of the health institutions 202 (e.g., to download data packages including electronic health records and/or updates to electronic health records and to perform other such techniques), and communicate with the sharing cloud server 206 to upload encrypted health data and perform other techniques described herein.

The sharing cloud server 206 may include a device authentication service 226, a data storage engine 228, an access control storage 230, a health data storage 232, a data retrieval engine 234, an assets engine 236, an EHR authentication service 238, and a logging engine 242. Generally, the device authentication service 226 is used to authenticate users of the user devices 205 for accessing the service provider 104 and/or the EHR system 108. For example, the device authentication service 226 may use a two-way authentication or mutual authentication such as internet key exchange (IKE), secure shell (SSH), or transport layer security (TLS). In an example that uses TLS, a client-side X.509 certificate may be used to authenticate the identity of the client (e.g., a user device 205) to the server (e.g., the provider sharing cloud sever 206), and an X.509 certificate may be used to authenticate the server to the client. In some examples, the mutual authentication may include the use of usernames and passwords in addition to or instead of certificates. In some examples, the access control storage 230 may store credential data usable by the device authentication service 226.

The data storage engine 228 may be configured to receive encrypted health data from the user device 205 and store it in the health data storage 232. For example, the data storage engine 228 may include a set of method calls to communicate with the user device 205 and store the encrypted health data. The encrypted health data may be passed to the health data storage 232 using a Blob application programming interface (API) to push data to the health data storage.

The access control storage 230 generally stores credentials for health institutions and/or providers. Information in the access control storage 230 may be accessed by the provider admin 212 as part of when an EHR system 108 makes a request for health data storage 232.

As introduced herein, the health data storage 232 may be used to store encrypted health data obtained from the user device 205. The data retrieval engine 234 may be used to retrieve the encrypted health data from the health data storage 232 responsive to requests from a clinician user device 240 (e.g., an example of the user device 205) providing a dashboard 106. For example, the data retrieval engine 234 may use a Blob API to pull data from the health data storage 232.

The assets engine 236 is configured to manage assets of the sharing cloud server 206. This may include removing or otherwise deleting old or stale data in the health data storage 232. In some examples, such deletion may be part of a garbage collection routine, or may be requested or otherwise instructed by the user device 205. For example, the user device may change the way the health data is stored and the assets engine 236 may make the adjustments in the health data storage 232.

The EHR authentication service 238 is used to authenticate the clinician user device 240 and/or the dashboard 106. For example, the EHR authentication service 238 may use a decentralized authentication protocol such as OpenID to authenticate the clinician user device 240 and/or the dashboard.

The clinician user device 240 may be operated by a clinician or other authorized user to access the health data of the user. The dashboard 106, which may be presented by the clinician user device 240, may be an application such as web application accessible via a web browser of the clinician user device 240 or any other suitable application accessible by the clinician user device 240. In some examples, the dashboard 106 may be hosted by the EHR system 108 and may be the typical dashboard 106 used by the clinician to access electronic health records stored by the EHR system 108. To enable the dashboard 106 to view the health data from the service provider 104, as described herein, the dashboard 106 may be slightly modified to include a link, icon, or other graphical element to enable the clinician to see the health data loaded into the EHR using the techniques described herein. In some examples, EHR system 108 communicates with the health application 222 to authenticate the user of the user device 205. Such communications may occur using an existing Health Level Seven International Standard (HL7) such as Fast Healthcare Interoperability Resource (FHIR) standard describing data elements, data formats, and APIs for exchanging electronic health records. In some examples, the open source implementation of the FHIR standard, referred to as SMART on FHIR (Substitute Medical Applications, Reusable Technologies on FHIR), may be appropriate.

The user device 205 may include the health application 222 and the health record storage 224. As described herein, the health application 222 may be used to perform the techniques relating to storing and sharing health record data. The health record storage 224 may be used to store the health data that is shared, as described herein, and any other health record data.

Logging engine 242 may be used to log transaction information related to requests for health care data received from the clinician dashboard 106 and/or the clinician user device 240, as described in further detail herein. In some examples, the logging engine 242 may also include encryption and/or decryption algorithms for performing cryptographic functions, as described herein. The logging engine 242 may store transaction information in the log 128, as introduced herein.

Figure 3:
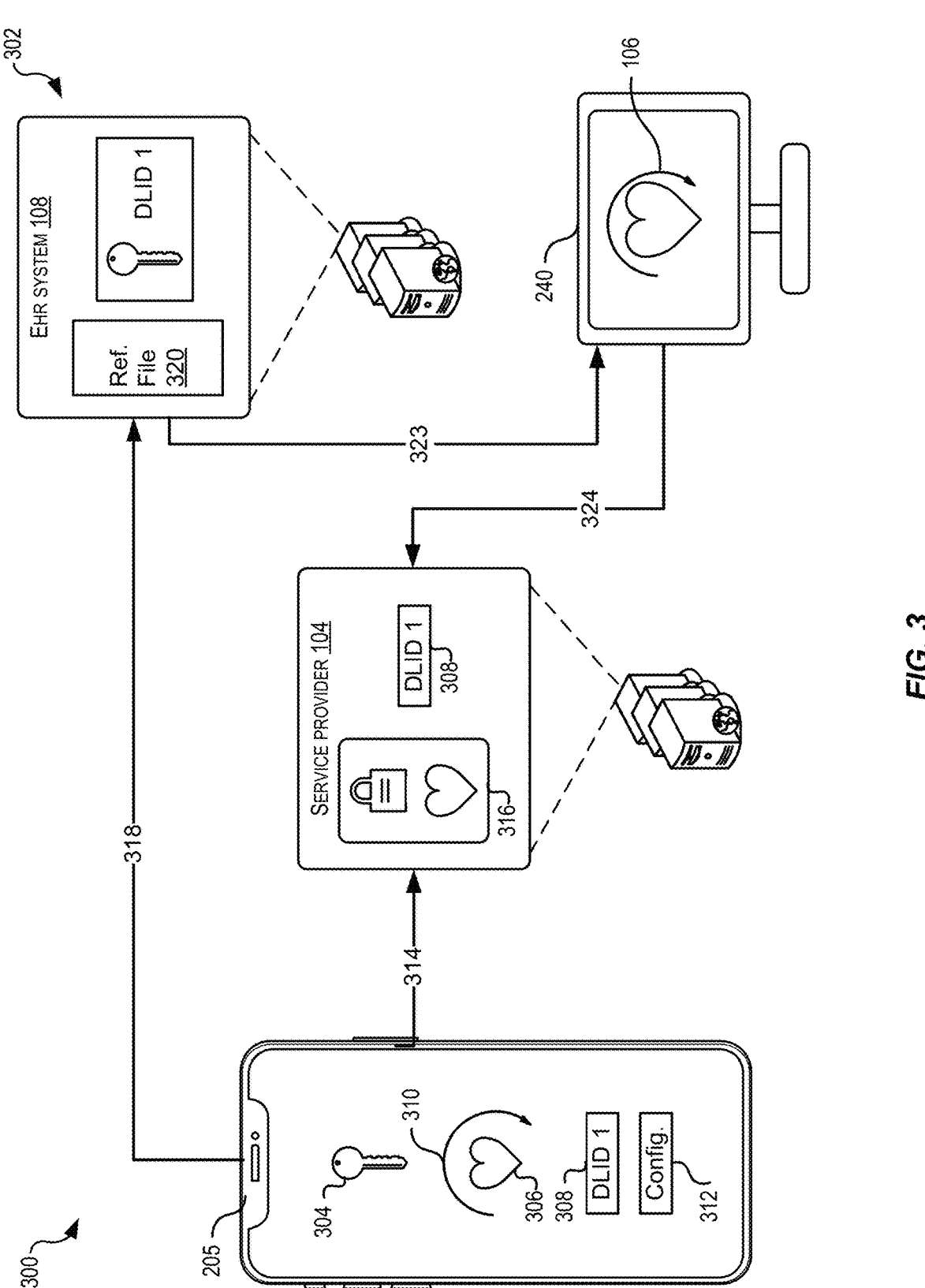
FIG. 3 illustrates a block diagram showing an example system and an example process for sharing health data by and among systems, according to at least one example.

FIG. 3 illustrates a block diagram showing an example system 302 and an example process 300 for sharing health data from user devices with electronic health record systems, according to at least one example. In particular, FIG. 3 depicts aspects of end-to-end encryption of the data within the system 302. The system 302, which is an example of the system 200, includes the user device 205, the service provider 104, the EHR system 108, and the clinician user device 240, which may include a version of the clinician dashboard 106 presented thereon by the EHR system 108. FIG. 3 is included to depict graphically the flow of cryptographic key(s) 304 (e.g., the cryptographic keys 122), health data 306, and unique data identifiers 308 by and between the elements of the system 302.

FIG. 3 depicts how health data is shared with among the elements of the system 302. The subject of this specification relates to logging access to the health data after sharing has been initiated using the process 300 or some other comparable process. In some examples, the logging may occur, in part, at the user device 205, the clinician dashboard 106 executing on the clinician user device 240, and/or the service provider 104.

The process 300 begins at 310 by the user device 205 accessing a configuration file 312 to determine query information for running a query to identify health data 306, and encrypting the identified data using the cryptographic key 304 (e.g., a symmetric key). The configuration file 312 may define the different data categories, data types, and the like that can be shared using the techniques described herein. When triggered, according to a periodic schedule, or in any other manner, the user device 205 (e.g., the health application) may run a query to identify the relevant data that can be identified, encrypted, and shared. At least some of the health data 306 may be stored in accordance with the multi-node data storage structure. In some examples, once data has been shared with a health institution, the user device 205 may periodically update the data by running a query on the data, identifying differences, and sharing the new data. In some examples, the user device 205 may share all of the data, not just the differences between old and new.

At 314, the process 300 includes the user device 205 uploading the health data 306, now encrypted, and the unique data identifier 308 to the service provider 104. The encrypted health data is identified as 316. The unique data identifier 308 is a Lookup ID for at least one of the data nodes of the multi-node data storage structure (e.g., 114). In some examples, the unique data identifier 308 identifies the root data node of the multi-node data storage structure, which may enable identification of corresponding branch nodes.

At 318, the process 300 includes the user device 205 storing/updating a document reference file 320 on the EHR system 108 with the cryptographic key 304 and the unique data identifier 308. In some examples, this information may be sent to the EHR system 108 using one or more APIs provided by the EHR system 108. Once received, the EHR system 108 stores the cryptographic key 304 and unique data identifier 308 in association with each other.

At 323, the process 300 includes the clinician user device 240 retrieving the cryptographic key 304 and unique data identifier 308 from the EHR system 108. For example, the clinician user device 240 may call a method in the API associated with the document reference file 320 of the EHR system 108 to obtain the cryptographic key 304 and the unique data identifier 308. With the cryptographic key 304 and unique data identifier 308, the clinician user device 240, at 324, can retrieve the encrypted data node identified by the unique data identifier 308 by providing the unique data identifier 308 to the service provider 104. In response, the service provider 104 retrieves the data associated with the encrypted data node and sends it back to the clinician user device 240.

In some examples, the clinician user device 240 also provides a token (e.g., OpenID token) or other authentication information for authentication by the service provider 104. In some examples, authentication of the actual clinician who is using the clinician user device 240 may be the responsibility of the EHR system 108 or other internal system that is separate from the service provider 104. In other words, the service provider 104 may authenticate at a health institution level (e.g., confirm that the clinician user device 240 and/or the dashboard belong to a known and trusted health institution), not necessarily at a user level (e.g., that the clinician operating the clinician user device 240 is authorized to view the health data). In conclusion, at 326, the process 300 includes the clinician user device 240 decrypting the health data 306 using the cryptographic key 304.

Figure 4:
FIG. 4 illustrates a diagram showing an example multi-node data structure for storing health data, according to at least one example.

FIG. 4 illustrates a block diagram showing a multi-node data storage structure 400 for storing and sharing health data from user devices with electronic health record systems, according to at least one example. The multi-node data storage structure 400 is an example of a multi-node data storage structure used to store health record data for a patient of a health institution. The multi-node data storage structure 400 includes a plurality of nodes that include an institution node 402(*a*) (e.g., a root node), category nodes 404(*a*) and 404(*b*), and data nodes 406(*a*)-406(*d*). The category nodes 404 and the data nodes 404 may be considered branch nodes.

The institution node 402(*a*) represents a patient's data associated with a health institution 410(*a*). This is the health institution with which the health data has been shared. The institution node 402(*a*) is encrypted with Key 0 and is uniquely identified by unique data identifier (DLID) 0. The unique data identifier may be generated by hashing the data stored at the corresponding node. In this manner, the DLID may be dynamic in nature and updated when the data at the node changes.

The institution node 402(*a*) includes data organized by one or more categories (e.g., medications and heart rate), which correspond directly to the category nodes 404(*a*) and 404(*b*). For each category node 404, the institution node 402(*a*) stores a unique data identifier (e.g., DLID 1 and DLID 2) and a key (e.g., Key 1 and Key 2). When a user desires to share the data represented by the multi-node data storage structure 400 with the health institution 410(*a*), key 0 and DLID 0 are shared with the health institution. This enables the health institution to identify the institution node 402(*a*) and decrypt the contents of the node to obtain DLID 1 and DLID 2 and corresponding Keys 1 and 2.

As illustrated, each category node 404 is uniquely identified by its DLID and is encrypted with its Key. For example, the category node 404(*a*) is identified by the DLID 1 and encrypted with Key 1. The medications category node 404(*a*) identifies one or more data ranges for which data of the data type "Medications" is stored by the multi-node data storage structure 400. For example, the medications category node 404(*a*) identifies data node 406(*a*) (e.g., medication Range 1 identified by DLID 3 and encrypted with Key 3) and data node 406(*b*) (e.g., medication Range 2 identified by DLID 4 and encrypted with Key 4). The heart rate category node 404(*b*) similarly identifies data ranges for which data of the data type "Heart Rate" is stored by the multi-node data storage structure 400. For example, the heart rate category node 404(*b*) identifies data node 406(*c*) (e.g., heart rate Range 1 identified by DLID 5 and encrypted with Key 5) and data node 406(*d*) (e.g., heart rate Range 2 identified by DLID 6 and encrypted with Key 6). The data from the data nodes 406 is used to populate the data views in a patient data area in a user interface.

Each data node 406 is used to store a sampling range and sampling frequency of data of the corresponding data type. For example, the heart rate Range 1 of data node 406(*c*) may correspond to a month's worth of data sampled weekly. The heart rate Range 2 of the data node 406(*d*) may correspond to a week's worth of data sampled daily or more frequently. The values for the different ranges may be stored by the data nodes 406. Of course, different sampling ranges and sampling frequencies are possible such as, for example, by years, months, quarters of years, weeks, days, hours, minutes, or seconds. In some examples, the data ranges may predefined by one or more clinicians, which, in some examples, may correspond to health care standard measurements (e.g., it may be standard to view heart rate over a daily period sampled every 30 minutes to identify daily peaks and valleys). In some examples, each data node 406 may be used to store one-time data, rather than data that is received at some frequency during some range. For example, the data node 406 may store an X-ray of a broken arm (e.g., a one-time event).

A configuration file 408 is used to generate the multi-node data storage structure 400. The configuration file 408 may define each medical category to be collected along with different combinations of sampling ranges and sampling frequencies. The user device 205 may reference the configuration file 408 as it collects and encrypts the multi-node data storage structure 400.

To generate the multi-node data storage structure 400, the user device 205 may begin by collecting and syncing data of the data nodes 406. The data nodes 406 and category nodes 404 may be synced with the service provider 104 as soon as they have been generated and/or may be queued and synced at some different frequency. The queues may be defined by size (e.g., as soon as 5 MB of data is ready, it is sent), by quantity of nodes (e.g., as soon as five nodes are ready, it is sent), or in any other suitable manner. The institution nodes 402(a) may be synced after all of the other nodes have been synced.

The multi-node data storage structure 400 graphically represents relationships between nodes, but should not be viewed as limiting. For example, nodes are illustrated as "connected" by dashed lines. While lower nodes (e.g., the root node) do reference higher nodes in the multi-node data storage structure 400, the data structure does not actually maintain associations directly between nodes. Thus, if one node were obtained by a nefarious user, that user would be unable to obtain other nodes.

Figure 5:
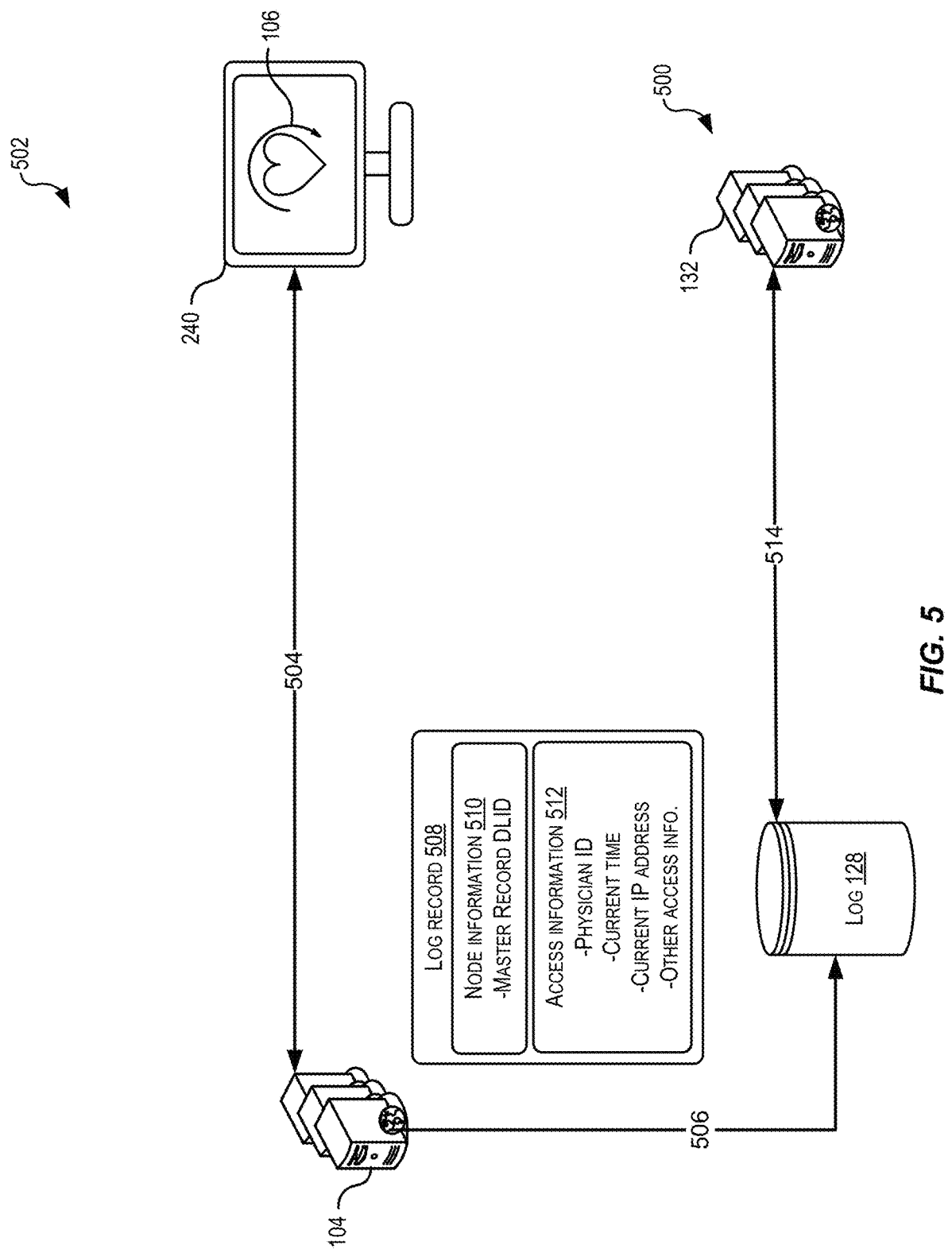
FIG. 5 illustrates a block diagram showing an example system and an example process for logging transaction data associated with accessing health data, according to at least one example.

FIG. 5 illustrates a block diagram showing an example system 502 and an example process 500 for logging transaction data associated with accessing health data, according to at least one example. In particular, FIG. 5 depicts an embodiment in which the service provider 104 is primarily responsible for logging transactions and, when requested, generating records of logged transactions and shares the same with the appropriate system.

The system 502, which is an example of the system 200, includes the clinician user device 240, which may include a version of the clinician dashboard 106 presented thereon by the EHR system 108 (not shown in FIG. 5), the service provider 104, the requesting system 132, and the log 128, which is operated by the service provider 104.

The process 500 begins at 504 by the clinician dashboard 106 requesting and receiving health data from the service provider 104. Prior to doing so, the clinician dashboard 106 may have been authorized by the EHR system 108 to confirm that the credentials of the user using the clinician dashboard 106 are authorized to access the service provider 104. The clinician dashboard 106 may then contact the service provider 104 with an OpenID token and a DLID of the root node of interest (e.g., a node associated with a patient of a health institution). In response, the service provider 104 may validate the OpenID token and generate an access token containing the DLID for the root node. Once the clinician dashboard 106 receives the access token, the clinician dashboard may make the request at 504 for health data by sending, in the request, the access token and the DLID of the root node to the service provider 104.

The health data may be stored in the multi-node data structure, as described with respect to FIG. 4. The service provider 104 may have obtained the health data from a user of a user device, as described with respect to FIG. 3. While the service provider 104 may store the health data of the user, the identity of the user is unknown to the service provider 104 because of the way the data is stored using the multi-node data structure. Thus, at 504, when the clinician dashboard 106 requests health data, the service provider 104 provides the clinician dashboard 106 with sufficient information to enable the clinician dashboard 106 to access a root node of health data. For example, the clinician dashboard 106 may include a document lookup identifier (DLID) in its request to the service provider 104, and the service provider 104 may use the DLID to access certain information to send back to the clinician dashboard. This DLID may identify the root1 node of the multi-node data structure used to store the health data. In some examples, additional exchanges may include additional DLIDs for lower-level nodes as the clinician dashboard 106 traverses the structure from node to node.

At 506, the process 500 includes the service provider 104 recording information associated with the request/response exchange with the clinician dashboard, described at 504, in the log 128. This may include the service provider 104 generating a log record 508 and storing the log record in the log database 128. The log record may be generated by extracting a physician identifier from the OpenID token and logging the physician identifier, DLID of the root node, timestamp, health institution identifier, IP address of the device that accessed the data, and any other suitable information. In some examples, the log record 508 may include node information 510 and access information 512. The log record 508 may include sufficient information to enable reconstruction by an entity other than the service provider 104 of which DLIDs were accessed by which users (e.g., by which physician identifiers) and when the ULIDs were accessed.

The node information 510 may identify which DLID was requested by the clinician dashboard 106. In some examples, a log record is generated each time a request is received that includes a DLID and information regarding the request, e.g., the requesting user and the time of the request. In this manner, there may be a one to one correspondence between log records and DLID access events. In some examples, the correspondence may be one to many. For example, if a series of requests are received that are related to the same root DLID, the remaining DLID access events (e.g., of lower-level nodes) may also be stored in the same log record 508. In any event, the log record 508 may include sufficient information to enable reconstruction of which DLIDs were accessed by which users (e.g., by which physician identifiers).

The access information 512, which may also be generated by the service provider 104 in response to receiving the request at 504, may include information relating to accessing the node identified by the DLID in the node information 510. In this manner, the access information 512 may include information such as, for example, physician identifier (e.g., an identifier that identifies a user of the health institution such as a physician, nurse, or any other health care professional), a current time (e.g., a time associated with when the request at 504 was received and/or processed), a current IP address (e.g., an IP address associated with the request at 504), and any other information associated with the request.

At 514, the process 500 includes the requesting system 132 requesting and receiving transaction information associated with the log record 508 and/or other log records generated by the service provider 104 and stored in the log 128. For example, the requesting system 132 may send a request to the service provider 104 for information about transactions between the service provider 104 and the clinician dashboard 106. The request may include a set of search parameters, which can be used by the service provider 104 to formulate a search query for querying the log 128. As much of the information stored by the log 128 may be encrypted, the search query may be vague with respect to the log 128. The requesting system 132 will need to decrypt the retrieved information and filter out data irrelevant to its request. Example parameters may identify one or more user identifiers (e.g., a physician identifier corresponding to the "physician ID" field in the access information), a time period corresponding to the "current time" field in the access information 512, one or more IP addresses corresponding to the "current IP address" field in the access information 512, and any other suitable information corresponding to any other fields in the log record 508. In some examples, the one or more user identifiers may be identifiers of users that are not physicians. The service provider 104 may conduct the search query and generate a data package that includes the results. As part of 514, the service provider 104 may share the data package with the requesting system 132. The requesting system 132 may also obtain an additional dataset from the health institution, e.g., the EHR system that provides the clinician dashboard 106 and that identifies a mapping between the node information and patient identifiers. With this additional dataset, the requesting system 132 can compare the records in the data package with the additional dataset to determine which patient records, were accessed by which physician (or at least which physician's ID if improperly used by another), and when. In this manner, the data package is configured to enable the requesting system 132 to identify, at a node level, which patient's records were accessed.

Figure 6:
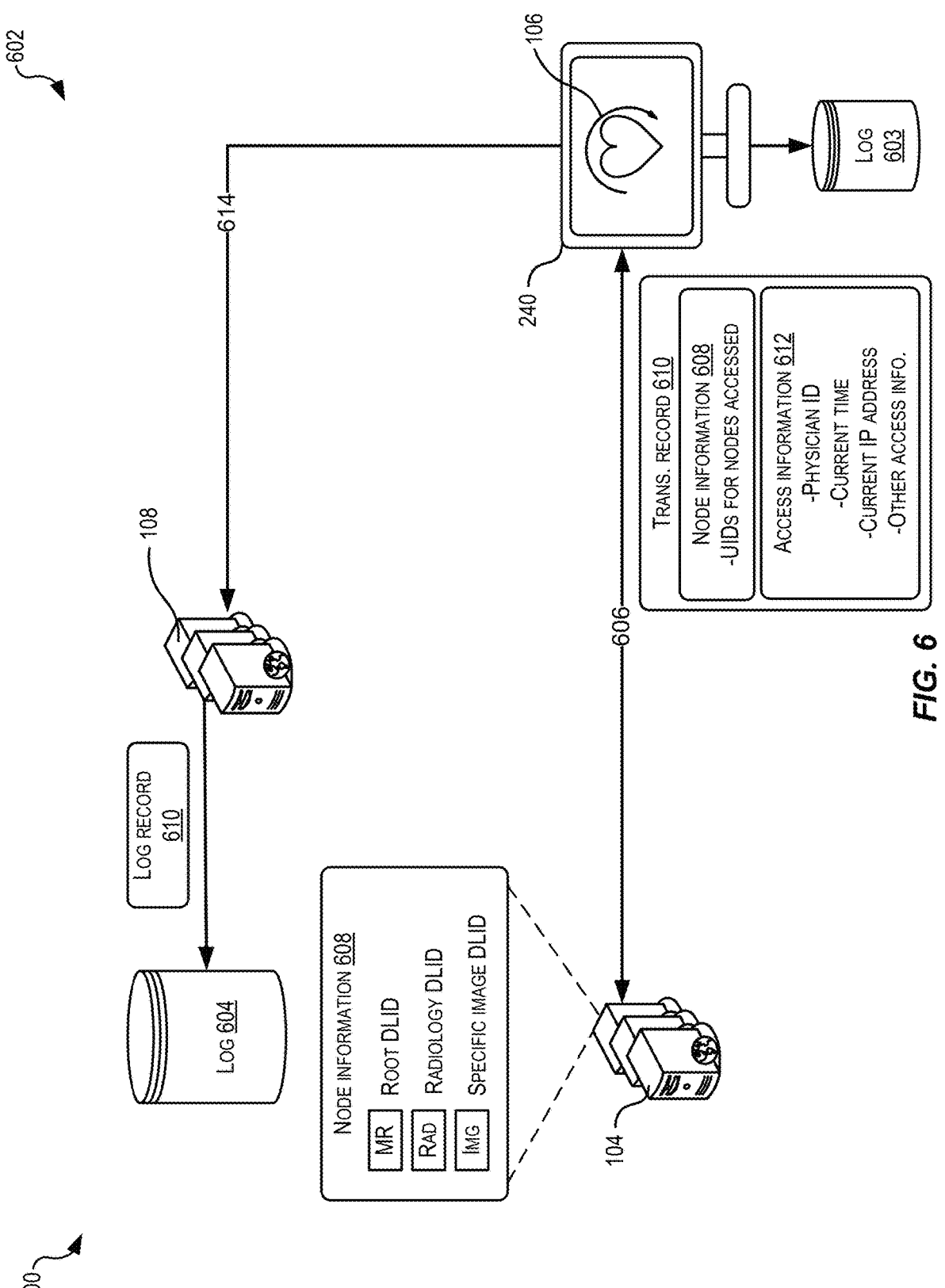
FIG. 6 illustrates a block diagram showing an example system and an example process for logging transaction data associated with accessing health data, according to at least one example.

FIG. 6 illustrates a block diagram showing an example system 602 and an example process 600 for logging transaction data associated with accessing health data, according to at least one example. In particular, FIG. 6 depicts an embodiment in which the clinician dashboard 106 is primarily responsible for logging transactions and shares information about logged transactions with the health institute/ EHR system 108 that implements the clinician dashboard 106.

The system 602, which is an example of the systems 200 and 502, includes the clinician user device 240, which may include a version of the clinician dashboard 106 presented thereon by the EHR system 108, a clinician dashboard log 603, the service provider 104, and an EHR log 604, which is operated by the EHR system 108.

The process 600 begins at 606 by a physician using the clinician dashboard 106 provided at the clinician user device 240 to access health data stored by the service provider 104 using a multi-node data structure, as described in further detail in FIG. 3 and FIG. 5. As an example, a record of accessing the health data may be represented as node information 608. The node information 608 may include master record (MR) information stored at a root node, a category node referred to as a radiology (RAD) node, and a data node that depicts a radiological image of left femur of the patient referred to as an image (IMG) node. As part of requesting the health data, the clinician dashboard 106 may provide the DLID for the root node. This node corresponds to a patient of the health institution, which is associated with the physician making the requests. The root and IMG node correspond to specific information stored under the root node.

As part of 606, the clinician dashboard 106 may generate a transaction record 610 using the node information 608 (e.g., information about which nodes were accessed at the service provider 104) and access information 612 (e.g., other information associated with the node information), which is similar to access information 512. The clinician dashboard 106 may store the transaction record 610 at the clinician dashboard log 603. In some examples, the clinician dashboard log 603 may be used for temporary storage of the transaction record 610. This is because, at 614, the clinician dashboard 106 may share the log record with the EHR system 108 for storage in the EHR log 604. In some examples, the communications between the clinician dashboard 106 and the EHR system 108 may be encrypted using any suitable protocol such as over Transport Layer Security (TLS) or other suitable protocol.

FIGS. 7A-7G illustrate a block diagram showing an example system 702 and an example process 700 for logging transaction data associated with accessing health data, according to at least one example. In particular, FIG. 7 depicts an embodiment in which multiple devices and systems are responsible for logging transactions, encrypting and decrypting information about logged transactions in connection with requests for such information.

The system 702, which is an example of the systems 200, 502, and 602, includes the clinician user device 240, which may include a version of the clinician dashboard 106 presented thereon by the EHR system 108, the log 128, the service provider 104, and the user device 205.

The process 700 begins at 704 by the user device 205 creating health data records 706 for health data that is generated by the user device 205 and/or obtained by the user device 205 from a different system. For example, the user device 205 and the system 200 may be used by a user of the user device 205 (e.g., a patient) to connect to an endpoint of the EHR system 108 (and other EHR systems) and download health record data associated with the patient. An application running on the user device 205, e.g., a health application, may include one or more algorithms to process the health record data to create health data records 706 and store the health data records 706 on the user device 205. This may include storing the health data records 706 according to the multi-node data structure discussed with reference to FIG. 4. When stored in this manner, each node may be identified by a DLID (e.g., the unique node identifier) and the content thereof may be encrypted using a unique encryption key. This encryption key is different from the encryption keys described with reference to FIG. 7. In the example depicted in FIG. 7A, the created health data records 706 may include master record (MR) information stored at a root node, a category node referred to as a radiology (RAD) node, and a data node that depicts a radiological image of left femur of the patient referred to as an image (IMG) node.

Figure 7B:
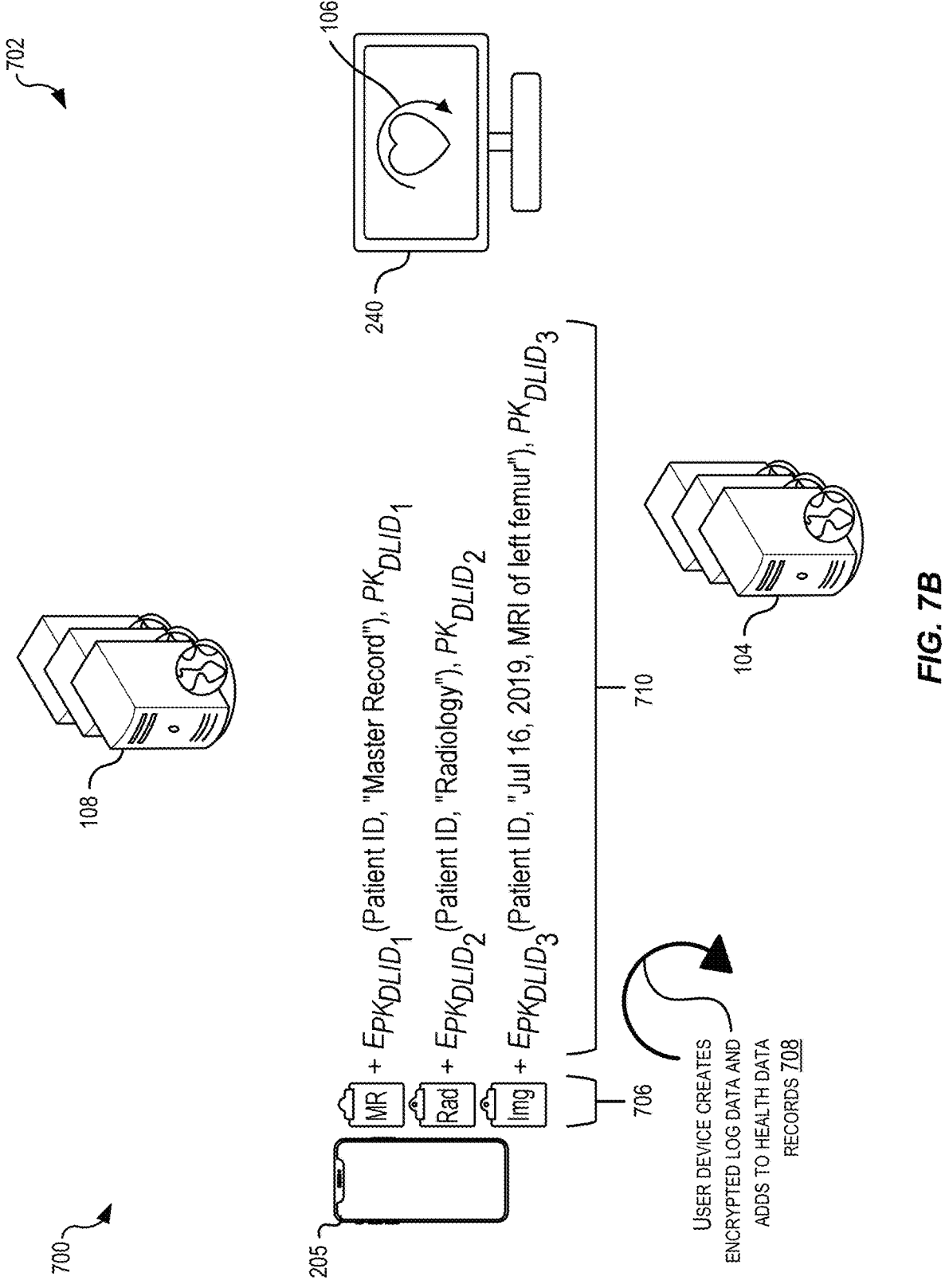

Turning now to FIG. 7B, this figure depicts 708 of the process 700. In particular, at 708, the process 700 includes the user device 205 creating encrypted log data 710 and adding the log data to health data records 706 generated at 704 (e.g., appends the log data to the records). In this example, for each node, the encrypted log data may include a unique patient identifier associated with the health data (e.g., patient ID) and a description of the health record data (e.g., "Master Record," "Radiology", etc.). The encrypted log data 710 for each node may be encrypted using a public key that is generated by the user device 205 and is unique to the respective node (e.g., PKDLID1, PKDLID2, etc.). In this manner, the log data of each node may be encrypted with its own public key. The user device 205 may store health data records 706 and encrypted log data 710 in a storage device of the user device 205 for a period of time and/or indefinitely. The user device 205 may utilize any suitable encryption algorithm to encrypt the log data that makes up the encrypted log data 710.

Figure 7C:
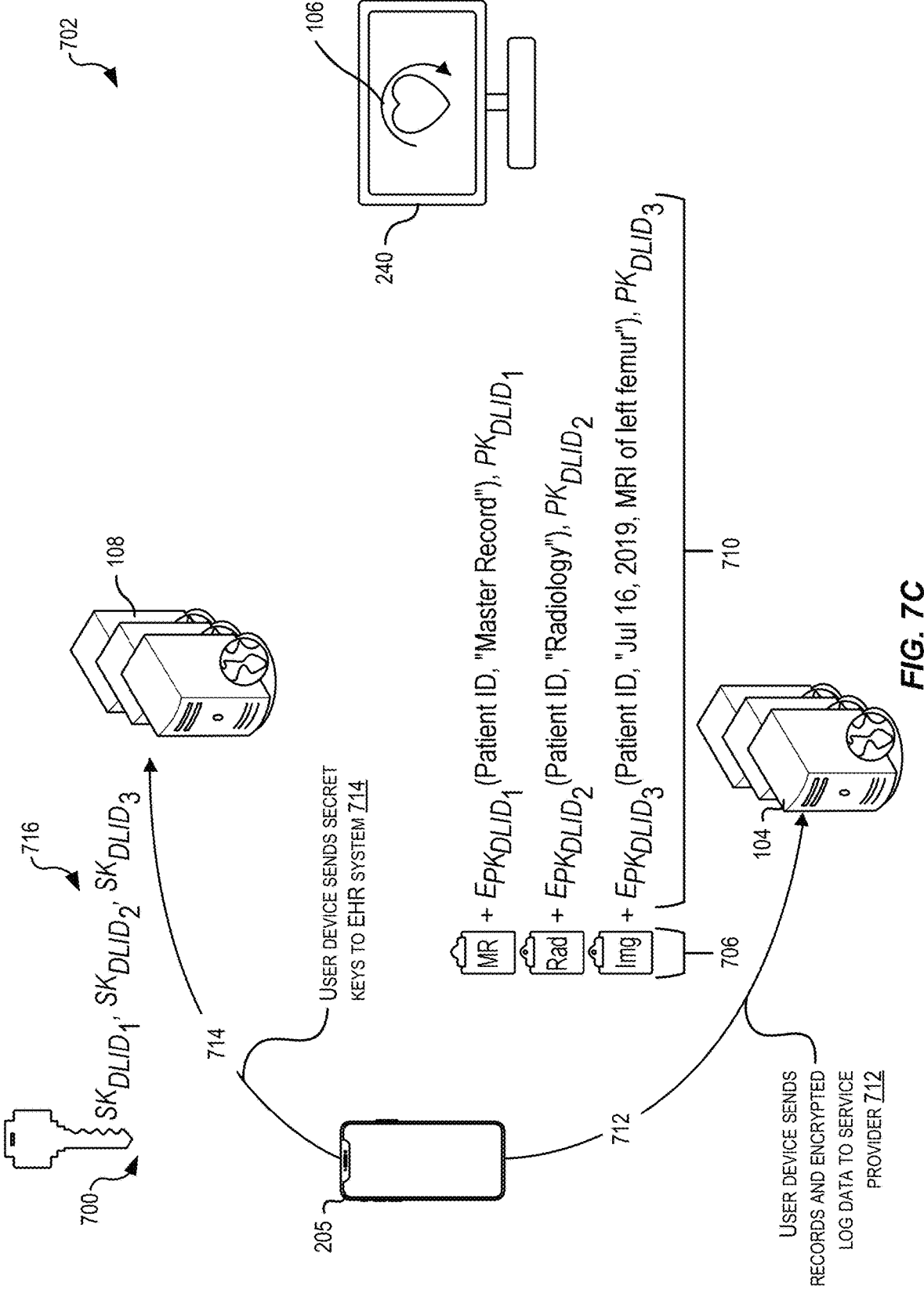

Turning now to FIG. 7C, this figure depicts 712 and 714 of the process 700. In particular at 712, the process 700 includes the user device 205 sending the health data records 706 and the corresponding encrypted log data 710 to the service provider 104. At 714, the user device 205 sends secret keys 716 (e.g., SKDLID1, SKDLID2, etc.) to the EHR system 108. The secret keys 716 correspond to the nodes that have been encrypted using the public keys (e.g., PKDLID1, PKDLID2). In some examples, the secret keys 716 may be usable to decrypt the encrypted log data 710. In some examples, the user device 205 generates the secret keys 716 and the public keys (e.g., key pairs) at or around the same time as the user device 205 generates the encrypted log data 710.

Figure 7D:
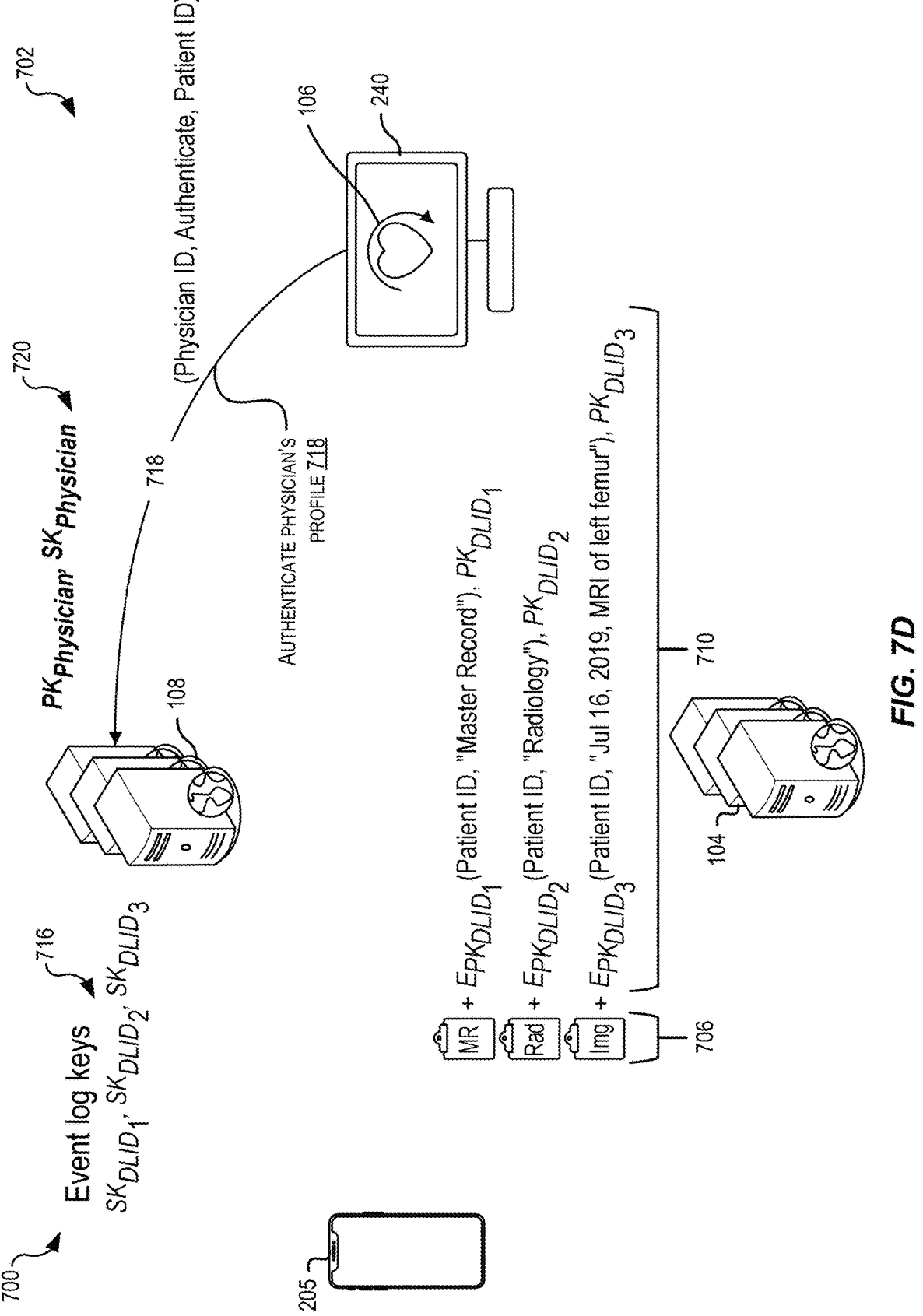

Turning now to FIG. 7D, this figure depicts 718 of the process 700. In particular, at 718, the clinician user device 240 including the clinician dashboard 106 is used to communicate with the EHR system 108 to authenticate a physician. This may include the clinician dashboard 106 sending, to the EHR system 108, a physician ID, a patient ID (e.g., an identifier of the patient whose record the patient is requesting access), and an authenticate request. In return, the EHR system 108 may authenticate the physician using any suitable authentication protocol including, for example, OpenID. In some examples, the clinician dashboard 106 also generates and provides to the EHR system 108 physician keys 720 (e.g., a physician public key (e.g., PK_{Physcian}) and a physician secret key (e.g., SK_{Physcian})).

Figure 7E:
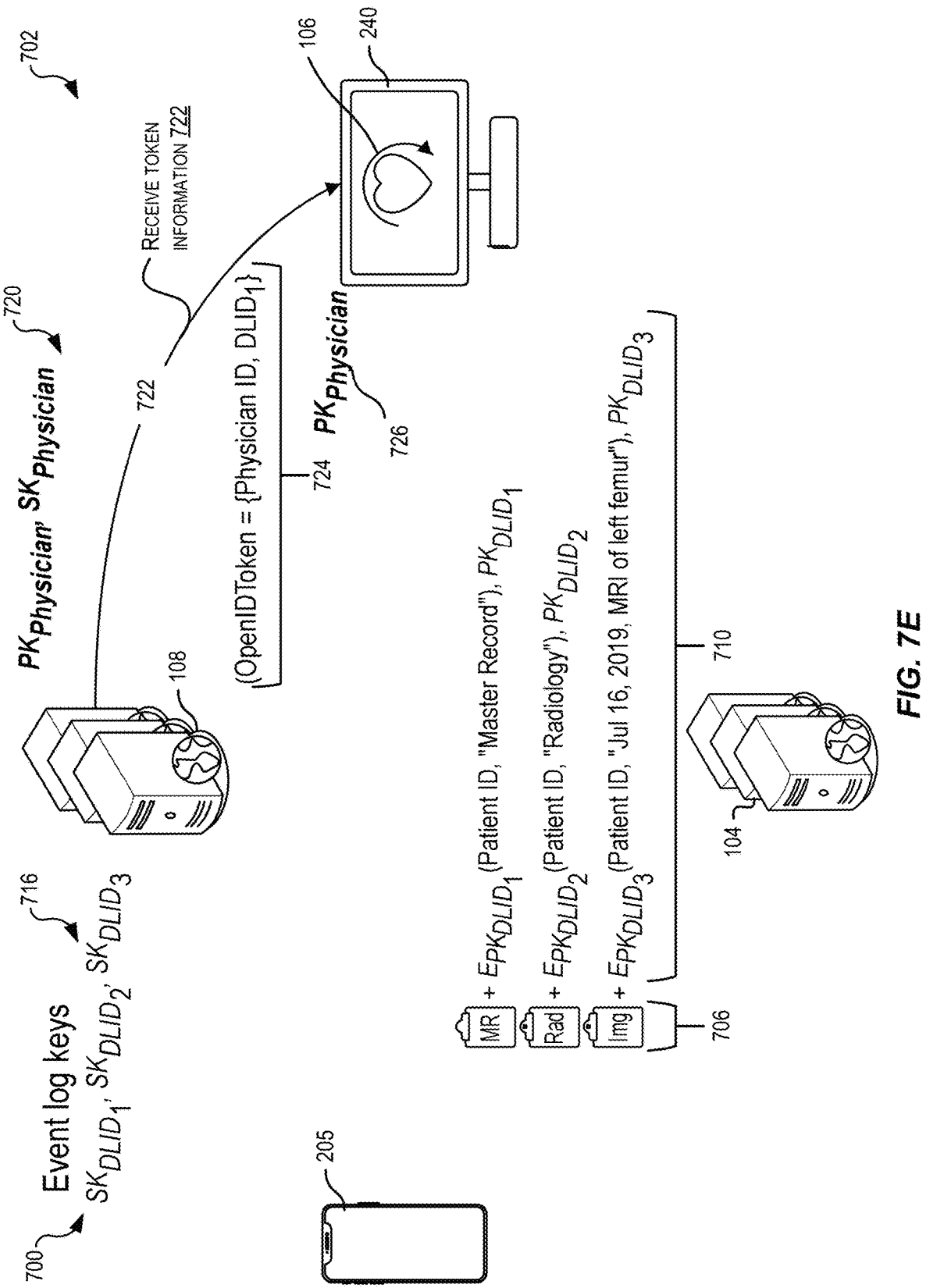

Turning now to FIG. 7E, this figure depicts 722 of the process 700. In particular, at 722, as part of authenticating the physician, the EHR system 108 returns token information 724 (e.g., OpenIDToken) to the clinician dashboard 106. The OpenIDToken may represent an access token that is based on the Physician ID (e.g., an identifier of the physician) and a DLID (e.g., the DLID for the root node for a patient identified by the Patient ID provided previously). The token information 724 may enable the user operating the clinician dashboard 106 to access health data from the service provider 104. In some examples, the EHR system 108 also sends the physician's public key (e.g., PK_{Physcian}) 726 to the clinician dashboard 106 at or about the same time as the EHR system 108 sends the token information 724 (e.g., as part of the same message) or as at a later or earlier time (e.g., as part of a different message). In some examples, the token information 724 may include the physician's public key 726 and, in some examples, the physician's secret key. Because the token information is signed by the EHR system 108 (e.g., at block 722), the token information may be certified by the EHR system 108.

Figure 7F:
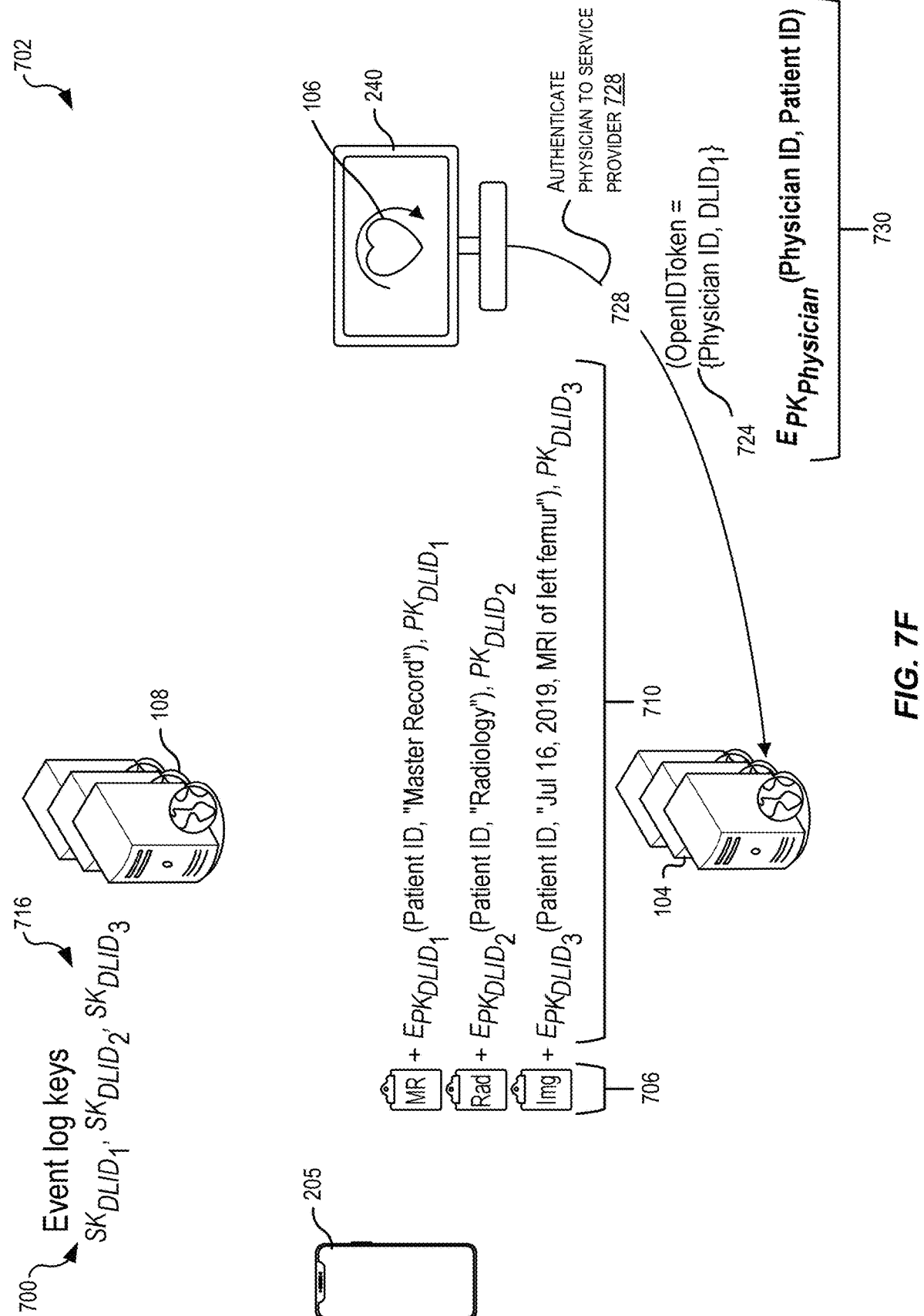

Turning now to FIG. 7F, this figure depicts 728 of the process 700. In particular, at 728, the process 700 includes authenticating the physician (e.g., the user of the clinician user device 240 at which the clinician dashboard 106 is operating) at the service provider 104. This may include the clinician dashboard 106 sending the token information 724

(e.g., the OpenIDToken) to the service provider 104. The token information may include the physician's public key 726. In some examples, the clinician dashboard 106 may also use the physician's public key 726 to generate encrypted IDs 730 by encrypting the Physician ID and Patient ID. The encrypted IDs 730 may also be sent to the service provider 104.

Figure 7G:
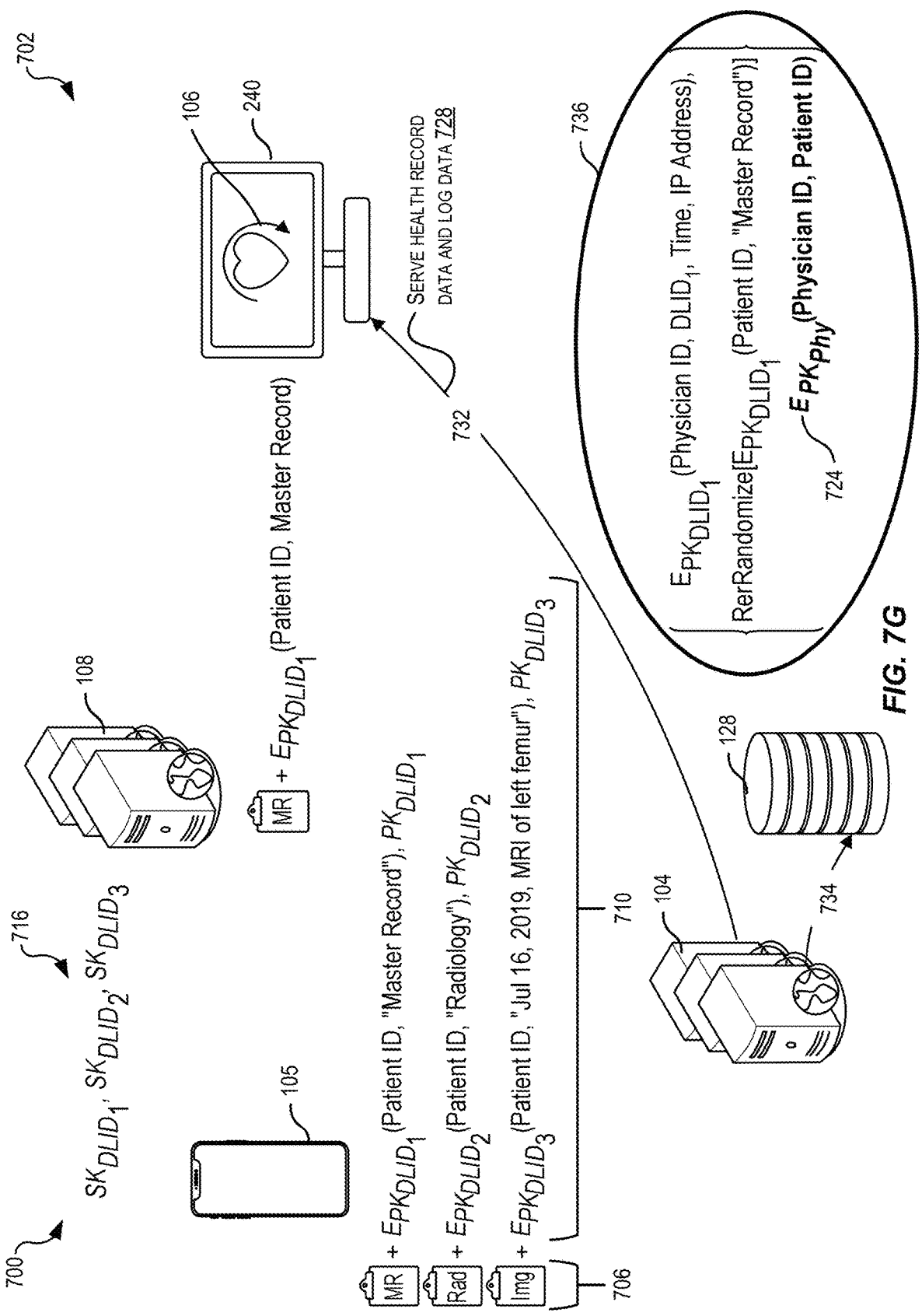

Turning now to FIG. 7G, this figure depicts 732 and 734 of the process 700. In particular, at 732, the process 700 includes the service provider 104 sending the health record data 706 and the encrypted log data 710 to the clinician dashboard 106. Because, at 728, the clinician dashboard 106 had provided the token information 724, at 732, the service provider 104 is able to use the token information 724 to identify which node (e.g., which patient) the physician is interested in viewing and serve the appropriate health record data 706(1) and the corresponding log data 710(1) to the clinician dashboard 106.

At 734, the process 700 includes the service provider 104 generating a log entry 736 corresponding to 732. In particular, the log entry 736 may include transaction information relating to the transaction that occurred when the clinician dashboard 106 requested and received data about a patient. The log entry 736 may be created and stored in the log 128, described herein. The log entry 736 may include transaction information (e.g., Physician ID, DLID_1, Time, IP Address) that is encrypted using the public key corresponding to respective DLID_1. The log entry 736 may be rerandomizable using the Patient ID and "Master Record"). For example, without decrypting or needing access to the secret-key (but with access to the public-key), the service provider 104 may take a ciphertext C and derive a new ciphertext C' that is unsinkable to C, but which decrypts to the same value. This ensures that someone looking at this log entry does not know which DLID record it corresponds to. In some examples, the log entry 736 may also include the encrypted IDs 730 (e.g., identifier information for the patient and the physician that has been encrypted using the physician's public key). In this example, the log entry 736 may be included in a row having a tuple of information.

Figure 8A:
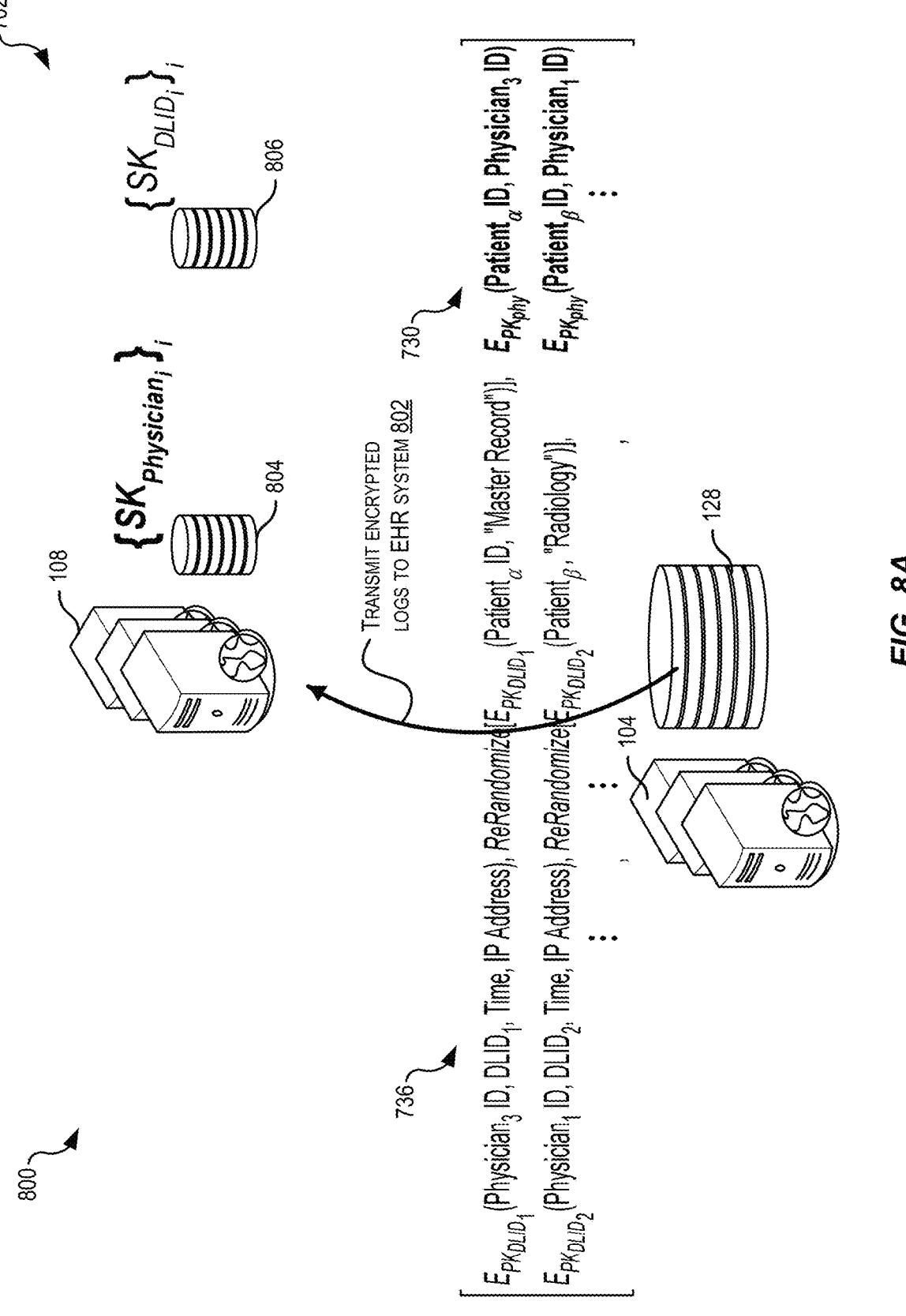
Figure 8B:
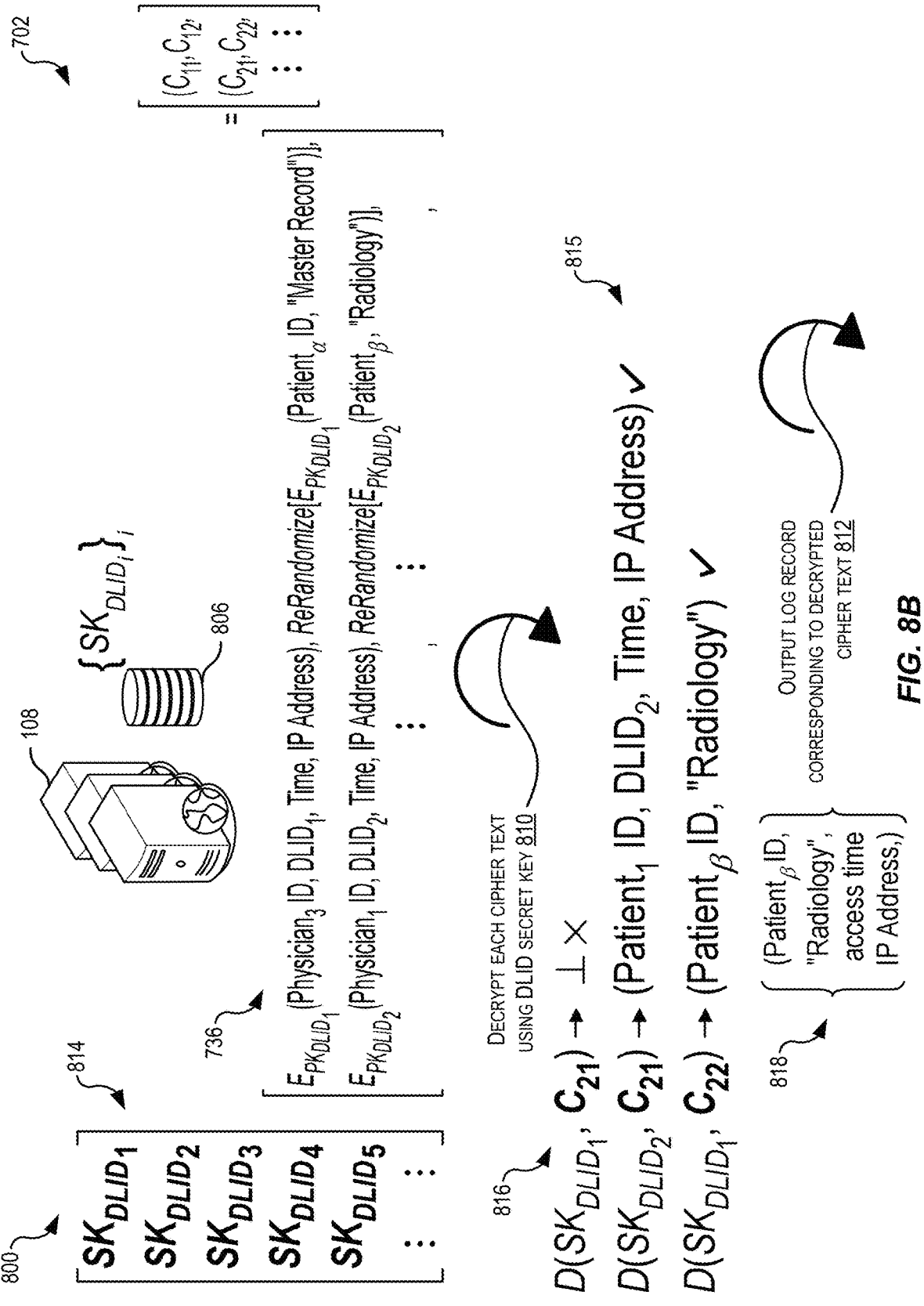

FIGS. 8A-8C illustrate a block diagram showing the system 702 and an example process 800 for sharing and decrypting logged transaction data associated with accessing health data, according to at least one example. In particular, FIG. 8 depicts multiple embodiments in which logged transaction data can be decrypted in order to identify who accessed what records and when.

The process 800 begins at 802 by the service provider 104 transmitting encrypted log data to the EHR system 108. For example, the encrypted log data (e.g., the multiple log entries 736) may be requested by the EHR system 108 as part of a responding to a security incident. For example, the EHR system 108 (e.g., a health institution associated with the EHR system 108) may learn of suspected or actual suspicious activity with respect to users accessing the health data stored by the service provider 104. In response, the health institution may want to learn which physician IDs (e.g., which physician profiles) were used to access what data (e.g., which nodes in the multi-node data structure) of which patientIDs (e.g., which patients of the health institution) and when (e.g., a time frame). In some examples, the service provider 104 may query the log 128 for relevant information, which may then be provided to the EHR system 108 at 802. In some examples, the service provider 104 also transmits the ciphertext corresponding to the encrypted log data 736. This may enable the EHR system 108 to decrypt and filter the results.

As illustrated in FIG. 8A, the EHR system 108 may store the secret keys for the physician in key storage 804 and may store the secret keys for the DLIDs in key storage 806. As described in further detail herein, the EHR system 108 may use the keys from key storage 806 and/or 804 to decrypt the log entries 736.

Turning now to FIG. 8B, this figure depicts 810 and 812 of the process 800. FIG. 8B depicts an approach for decrypting the encrypted log data 736 that may be performed when the log data 736 does not include the third ciphertext in a tuple (e.g., the encrypted IDs 730). Because the EHR system 108 does not have the encrypted IDs 730, the EHR system 108 may have to expend additional computing resources to "brute force" decrypt the log data 736, as compared to the approach described with respect to FIG. 8C. In this case, "brute force" is used in the sense of decrypting with all possible keys uploaded to the EHR system 108 by clients (e.g., keys of the form SK_DLID_i). In some examples, this approach can be narrowed down to a particular user's SK_DLIDs if the focus is who has accessed a particular user's files.

At 810, the process 800 includes the EHR system 108 decrypting each ciphertext 808 (corresponding to the encrypted log data 736) using DLID secret keys 814 stored in the key storage 806. In some examples, 810 may be considered a brute force decryption technique as multiple attempts might be required before successfully decrypting a log entry 736. Arrow 815 identifies three examples of attempts to decrypt ciphertexts using DLIDs. The first attempt failed, but the second two were successful.

At 812, the process 800 includes the EHR system 108 outputting log records corresponding to the decrypted ciphertext. This may be identified by outputted log record 818. The outputted log record 818 may include the patientID, type or record ("radiology"), access time, IP address, and any other suitable information.

Turning now to FIG. 8C, this figure depicts 820, 822, and 824 of the process 800. FIG. 8C depicts an approach for decrypting the encrypted log data 736 that may be performed when the log data 736 includes the third ciphertext in tuple (e.g., the encrypted IDs 730). Even though the EHR system 108 includes the encrypted IDs 730, the EHR system 108 may nevertheless have to expend additional computing resources to "brute force" decrypt the log data 736 including multiple more possible combinations. In this case, "brute force" in used in the sense of decrypting with all possible keys uploaded to the EHR system 108 by clients (e.g., keys of the form SK_DLID_i).

At 820, the process 800 includes the EHR system 108 decrypting each third ciphertext in the tuple using the physician secret keys 826 stored in the key storage 804. For example, this may include using the physician secret keys 826 to decrypt the encrypted IDs 730. Arrow 828 identifies three examples of attempts to decrypt ciphertexts using physician secret keys 826. The first two attempts failed, but the third was successful. At 820, the only thing that is being decrypted is the third column, so this step is finished after a successful decryption has been logged.

Once the encrypted IDs 730 have been decrypted, at 822, the process 800 includes the EHR system 108 using the decrypted patient ID (e.g., from the encrypted IDs 730) to retrieve the corresponding DLID key 816 (e.g., from the key storage 806) in order to decrypt the remainder of the log data 736 (e.g., the first and second information elements in the tuple). In some examples, 822 may be performed with little to no trial and error. This is because the patient-physician mapping is known from the decrypted IDs 730, which enables the EHR system 108 to simply pick the correct DLID key 816 to decrypt the remainder of information in the log data 736.

Once all three information elements of the log entry 736 have been decrypted, at 824, the process 800 includes the EHR system 108 outputting log entry corresponding to decrypted ciphertext. This may be identified by outputted log record 830. The outputted log record 830 may include the patientID, type or record ("Radiology"), access time, IP address, and any other suitable information. Of course, the content of the outputted log record 830 will depend on what information is stored by the log record. At this point, the patient ID, the physician ID, which record was accessed, at what time, and from where is known. This may be helpful to identify compromised systems and to identify who must be notified about any possible data breaches.

FIG. 9 illustrates a flow chart showing an example process 900 for generating and sharing transaction data relating to a health data, according to at least one example. The process 900 may be performed by the logging engine 242 (FIG. 2) of the sharing cloud server 206 (FIG. 2) of the service provider 104 (FIG. 1).

The process 900 begins at block 902 by the service provider 104 storing health data for a plurality of users according to a multi-node data structure. In some examples, each user may have their own respective record of health data stored in their own multi-node data structure. Each node of the multi-node data structure may be encrypted with a unique encryption key and may be identified by a unique data identifier.

The health data may include clinical health record data, sensor data, and/or any other suitable type of health data. In some examples, the clinical health record data is received from the electronic health record system or from a different health record system associated with a different health institution. In some examples, the sensor data is generated by a sensor of the mobile user device or received from a different user device (e.g., accessory device such as a watch, wearable monitor) associated with the mobile user device. In some examples, a first portion of the health data is obtained by the mobile user device from the electronic health record system, and a second portion of the health data is obtained by the mobile user device from a different electronic health record system associated with a different health institution. In some examples, the health data is organized into a plurality of categories. In this example, the multi-node data storage structure may include a root node that represents the health institution and a plurality of branch nodes corresponding to each of the plurality of categories.

In some examples, the root node may be associated with the patient profile. The root node may be linked to other nodes that store other health data associated with the patient profile. In some examples, the root node may be assigned to a unique health institution responsible for maintaining health records for a patient to which the patient profile belongs At block 904, the process 900 includes the service provider 104 receiving a first request to access a portion of the health data. The first request may be received from a clinician dashboard (e.g., 106) associated with a health institution and provided by the service provider 104. The first request may constitute a data access request and may include (i) a particular unique data identifier associated with a particular node of the multi-node structure, and (ii) a user identifier associated with a health care professional of the health institution.

At block 906, the process 900 includes the service provider 104 generating a transaction record based at least in part on logged information associated with the first request. The transaction record may identify (i) the particular unique data identifier, (ii) the user identifier associated with the user of the health institution, and (iii) metadata associated with the first request. The transaction record is an example of an entry in a transaction record.

In some examples, receiving the first request may include receiving token information. In this example, generating the transaction record may be based at least in part on the logged information associated with the first request by extracting at least the user identifier from the token information. The token information may be generated by the EHR system.

At block 908, the process 900 includes the service provider 104 storing the transaction record in a database. The database may be accessible to the service provider. In some examples, the database may be the log 128. The database may include other transaction records associated with other requests to access the health data. The transaction record may be configured to prevent the service provider 104 from identifying the patient profile associated the particular unique data identifier or a health care professional profile associated with the health care professional.

At block 910, the process 900 includes the service provider 104 querying the database in response to receiving a second request to access the transaction data. The querying may be performed in accordance with information received in the second request (e.g., SK_DLID). The information may identify one or more search parameters such as an identity of a health institution associated with the particular unique data identifier, a physician identifier (e.g., the user identifier), a range of time, an IP address, a patient identifier, and/or any other suitable type of information.

At block 912, the process 900 includes the service provider 104 generating a data package based at least in part on search results generated by querying the database. In some examples, the data package may include the transaction record or some form of transaction information based on the data package. The transaction record may be saved in plain text and/or may be encrypted.

At block 914, the process 900 includes the service provider 104 sending the data package to an external system associated with the second request. The external system may be external with respect to an operator of the service provider 104. In some examples, the external system may include a system or device associated with the EHR system and/or the health institution. The second request may have been sent to obtain information about which physicians have been accessing which patient records and when. For example, as part of a security breach, the health institution may need to find out which physician's profile (e.g., credentials) were being used to access patient records to determine whether the use was legitimate or illegitimate.

The data package may include the transaction record. The transaction record may be configured to enable the external system to identify a patient profile associated with the particular unique data identifier and the health care professional profile associated with the health care professional. In some examples, the transaction record alone is insufficient to identify the patient profile. In this manner, the identity of the patient is obscured from the service provider, but determinable by the external system because the external system may maintain a mapping of physician identifiers to information associated with a patient (e.g., patient identifier, unique data identifier (e.g., DLID)).

FIG. 10 illustrates a flow chart showing an example process 1000 for generating and sharing transaction data relating to a health data, according to at least one example.

The process 1000 may be performed by the health application 222 (FIG. 2) of the user device 205 (FIG. 2). The blocks of process 1000 generally correspond to the discussion with respect to FIGS. 7A-7C.

The process 1000 begins at block 1002 by the user device 205 obtaining health data. In some examples, the health data may include clinical health record data, sensor data, and/or any other suitable type of health data. In some examples, the clinical health record data is received from the electronic health record system or from a different health record system associated with a different health institution. In some examples, the sensor data is generated by a sensor of the mobile user device or received from a different user device (e.g., accessory device such as a watch, wearable monitor) associated with the mobile user device. In some examples, a first portion of the health data is obtained by the mobile user device from the electronic health record system, and a second portion of the health data is obtained by the mobile user device from a different electronic health record system associated with a different health institution.

At block 1004, the process 1000 includes the user device 205 generating health data records. This may include processing the health data, encrypting the health data, formatting the health data, and/or storing the health data on the user device 205. For example, the health data may be stored on the user device 205 using a multi-node data storage structure (e.g., FIG. 4). In this example, each node of the multi-node data structure may be identified by a unique data identifier. In some examples, the health data is organized into a plurality of categories. In this example, the multi-node data storage structure may include a root node that represents the health institution and a plurality of branch nodes corresponding to each of the plurality of categories. In some examples, the process 1000 may include encrypting the health data associated with a user account of the user device 205. In some examples, encrypting the health data may be performed using a plurality of cryptographic keys. Encrypting the health data may include encrypting each node of a multi-node storage structure by which the health data is stored and using a unique cryptographic key of a plurality of cryptographic keys.

At block 1006, the process 1000 includes the user device 205 generating cryptographic keys. The cryptographic keys may represent public keys for each data node identifiers (DLIDs) of each node of the multimode data structure.

At block 1008, the process 1000 includes the user device 205 encrypting log data corresponding to the health data records. For example, the user device 205 may use the generated public keys to encrypt information including the patient identifier and information about the record (e.g., the name of the node at which the record is saved). In an example case, block 1008 may include encrypting the patient ID and "Master Record" using the public key for DLID1 (e.g., the root node), encrypting the patient ID and "Radiology" using the public key for DLID2 (e.g., the node in the next level), and encrypting the patient ID and "Jul. 16, 2019, MRI of left femur using the public key for DLID3 (e.g., the node in the level below DLID2). Once encrypted, the log data may be appended or otherwise associated with the stored health data records, generated at 1004.

At block 1010, the process 1000 includes the user device 205 sending event log keys to the EHR system 108. This may include sending the secret keys corresponding to the public keys for the DLIDs described with respect to block 1012. The EHR system 108 may be a completely different from the user device 205 and the service provider 104. In some examples, the EHR system 108 may maintain the keys and use them when a request is made to decrypt the log data.

At block 1012, the process 1000 includes the user device 205 sending health data records and encrypted log data to service provider 104. This may include sending this data out of band or in response to a request for such data.

FIG. 11 illustrates a flow chart showing an example process 1100 for authenticating physician user of a first system to access health data from a second system, according to at least one example. The process 1100 may be performed by the clinician dashboard 106 (FIG. 1) operating on the clinician user device 240 (FIG. 2). The blocks of process 1100 generally correspond to the discussion with respect to FIGS. 7D-7G.

The process 1100 begins at block 1102 by the clinician dashboard 106 sending authenticating information to the EHR system 108. The authenticating information may include, for example, a physician identifier, an authentication request, and a patient identifier. The EHR system 108 in return may determine whether the physician identified by the physician identifier is authorized to view health data of a patient identified by the patient identifier. In some examples, the EHR system 108 may be primarily responsible for authenticating users, which, when authenticating, may request health data from the service provider 104.

At block 1104, the process 1100 includes the clinician dashboard 106 receiving token information and key information from the EHR system 108. In some examples, the token information may include an OpenIDToken that includes a physician identifier and a node identifier (e.g., DLID, which also can be used to identify a patient). The key information, which in some examples, is not sent by the EHR system 108, may include a public key for the physician. In some examples, the key information is included in the token information. For example, the OpenIDToken may include the physician's public key and, in some examples, the physician's secret key as well.

At block 1106, the process 1100 includes the clinician dashboard 106 sending token information and key information to the service provider 104 for authentication. This may include forwarding the OpenIDToken to the service provider 104 as evidence that the clinician dashboard 106 has previously been authenticated by the EHR system 108 (e.g., the system that issued the token). The OpenIDToken also identifies which node DLID the clinician dashboard 106 is interested in accessing. In some examples, the key information provided by the clinician dashboard 106 may include the physician identifier and patient identifier encrypted using the physician's public key received at 1104. In some examples, this information may be used by the service provider 104 as part of maintaining the logs received from the user device 205 as part of process 1000.

At block 1108, the process 1100 includes the clinician dashboard 106 receiving health record data and encrypted log data from the service provider 104. In some examples, this may include a package of log data that is encrypted by the public key for the node (e.g., DLID) and using the patient identifier and node information (e.g., a root node). As part of receiving the health data, the clinician dashboard 106 may view the health data, run queries, and the like.

FIG. 12 illustrates a flow chart showing an example process 1200 for generating log entries based on requests and sharing log entry information based on requests, according to at least one example. The process 1200 may be performed by the logging engine 242 (FIG. 2) of the sharing cloud server 206 (FIG. 2) of the service provider 104 (FIG.

1). The blocks of process 1200 generally correspond to the discussion with respect to FIGS. 7G and 8A

The process 1200 begins at block 1202 by the service provider 104 recording log entries relating to requests to access health data. The requests may have originated from clinician dashboards 106 as described with respect to FIG. 11. In some examples, recording the log entries may include generating log entries based on information in the requests. For example, a log entry for a particular request to access a root node may include a row including first ciphertext, second ciphertext, and, in some examples, third ciphertext. The first ciphertext may include a physician identifier, a DLID for "root node," a time, and an IP address, all of which may be encrypted using a public key for the DLID. In some examples, the second ciphertext may be derived from a rerandomization of the second ciphertext based on the patient identifier and node description (e.g., "Master Record") encrypted using the public key for the DLID. The third ciphertext may include the patient identifier and physician identifier encrypted using the public key for the physician. The log entries may be stored in a log (e.g., any suitable database capable of storing a table of information).

At block 1204, the process 1200 includes the service provider 104 receiving a request from a requesting system to view log entries. In some examples, the receiving system may be associated with the EHR system 108, an agent of the health institution, or other any other suitable entity. In some examples, prior to receiving the request or as part of receiving the request, the external system may be subjected to authorization to confirm that the external system has appropriate rights to receive and/or view the log entries.

At block 1206, the process 1200 includes the service provider 104 identifying relevant log entries based on the request. This may include the service provider 104 identifying search parameters in the request and conducting a search of the log using the search parameters.

At block 1208, the process 1200 includes the service provider 104 providing the log entries to the requesting system. For example, the service provider 104 may generate a data package that includes the log entries and send the same to the requesting system.

FIG. 13 illustrates a flow chart showing an example process 1300 for decrypting log entries, according to at least one example. The process 1300 may be performed by the EHR system 108 (FIG. 1), the requesting system 132 (FIG. 1), or any other comparable computer system. The blocks of process 1300 generally correspond to the discussion with respect to FIGS. 8B and 8C.

The process 1300 begins at block 1302 by the EHR system 108 beginning decryption of log entries. Block 1302 may be performed after the EHR system 108 has received the log entries, e.g., from the service provider 104.

At block 1304, the process 1300 includes the EHR system 108 determining whether a first log entry includes a third ciphertext (e.g., the encrypted IDs 730). If no, the process 1300 proceeds to block 1306, at which, the process 1300 includes the EHR system 108 trying patient keys to decrypt log entry. This may include the EHR system 108 attempting different combinations of patient keys (e.g., DLID keys) with different ones of the first and second ciphertexts in the log entry.

At block 1308, the process 1300 includes the EHR system 108 outputting a log record. This may occur after the EHR system 108 successfully decrypts the ciphertexts, as described at block 1306. Outputting the log record may include generating a data package that includes the patient identifier, the record name (e.g., "Master Record"), the access time, and the IP address.

At block 1310, the process 1300 includes the EHR system 108 determining whether there are other log entries to decrypt. If no, the process 1300 ends at 1312. If yes, the process 1300 returns to block 1304. If the answer at block 1304 is yes, the process 1300 proceeds to block 1314. At block 1314, the process 1300 includes the EHR system 108 trying physician keys to decrypt a first portion of the log entry. The first portion may correspond to the third cipher-text. Once the first portion has been decrypted, the EHR system 108 may be able to determine the patient ID, which, at 1316 is used by the EHR system 108 to retrieve corresponding patient key (e.g., DLID key).

At 1318, the process 1300 includes the EHR system 108 using the patient key to decrypt remaining portions of the log entry (e.g., the first and second ciphertext). In some examples, the remaining portions may include more than the first and second ciphertexts.

After 1318, the process 1300 includes the EHR system 108 outputting log record based on the decrypted portions of the log entry.

FIG. 14 illustrates an example architecture or environment 1400 configured to implement techniques described herein, according to at least one example. In some examples, the example architecture 1400 may further be configured to enable a user device 1406 and service provider computer 1402 to share information. The service provider computer 1402 is an example of the service provider 104 and the EHR system 108. The user device 1406 is an example of the user devices 240 and 205. In some examples, the devices may be connected via one or more networks 1408 (e.g., via Bluetooth, WiFi, the Internet). In some examples, the service provider computer 1402 may be configured to implement at least some of the techniques described herein with reference to the user device 1406 and vice versa.

In some examples, the networks 1408 may include any one or a combination of many different types of networks, such as cable networks, the Internet, wireless networks, cellular networks, satellite networks, other private and/or public networks, or any combination thereof. While the illustrated example represents the user device 1406 accessing the service provider computer 1402 via the networks 1408, the described techniques may equally apply in instances where the user device 1406 interacts with the service provider computer 1402 over a landline phone, via a kiosk, or in any other manner. It is also noted that the described techniques may apply in other client/server arrangements (e.g., set-top boxes), as well as in non-client/server arrangements (e.g., locally stored applications, peer-to-peer configurations).

As noted above, the user device 1406 may be any type of computing device such as, but not limited to, a mobile phone, a smartphone, a personal digital assistant (PDA), a laptop computer, a desktop computer, a thin-client device, a tablet computer, a wearable device such as a smart watch, or the like. In some examples, the user device 1406 may be in communication with the service provider computer 1402 via the network 1408, or via other network connections.

In one illustrative configuration, the user device 1406 may include at least one memory 1414 and one or more processing units (or processor(s)) 1416. The processor(s) 1416 may be implemented as appropriate in hardware, computer-executable instructions, firmware, or combinations thereof. Computer-executable instruction or firmware implementations of the processor(s) 1416 may include computer-executable or machine-executable instructions written in any suitable programming language to perform the various functions described. The user device 1406 may also include geo-location devices (e.g., a global positioning system (GPS) device or the like) for providing and/or recording geographic location information associated with the user device 1406.

The memory 1414 may store program instructions that are loadable and executable on the processor(s) 1416, as well as data generated during the execution of these programs. Depending on the configuration and type of the user device 1406, the memory 1414 may be volatile (such as random access memory (RAM)) and/or non-volatile (such as read-only memory (ROM), flash memory). The user device 1406 may also include additional removable storage and/or non-removable storage 1426 including, but not limited to, magnetic storage, optical disks, and/or tape storage. The disk drives and their associated non-transitory computer-readable media may provide non-volatile storage of computer-readable instructions, data structures, program modules, and other data for the computing devices. In some implementations, the memory 1414 may include multiple different types of memory, such as static random access memory (SRAM), dynamic random access memory (DRAM), or ROM. While the volatile memory described herein may be referred to as RAM, any volatile memory that would not maintain data stored therein once unplugged from a host and/or power would be appropriate.

The memory 1414 and the additional storage 1426, both removable and non-removable, are all examples of non-transitory computer-readable storage media. For example, non-transitory computer-readable storage media may include volatile or non-volatile, removable or non-removable media implemented in any method or technology for storage of information such as computer-readable instructions, data structures, program modules, or other data. The memory 1414 and the additional storage 1426 are both examples of non-transitory computer-storage media. Additional types of computer-storage media that may be present in the user device 1406 may include, but are not limited to, phase-change RAM (PRAM), SRAM, DRAM, RAM, ROM, Electrically Erasable Programmable Read-Only Memory (EEPROM), flash memory or other memory technology, compact disc read-only memory (CD-ROM), digital video disc (DVD) or other optical storage, magnetic cassettes, magnetic tape, magnetic disk storage or other magnetic storage devices, or any other medium that can be used to store the desired information and that can be accessed by the user device 1406. Combinations of any of the above should also be included within the scope of non-transitory computer-readable storage media. Alternatively, computer-readable communication media may include computer-readable instructions, program modules, or other data transmitted within a data signal, such as a carrier wave, or other transmission. However, as used herein, computer-readable storage media does not include computer-readable communication media.

The user device 1406 may also contain communications connection(s) 1428 that allow the user device 1406 to communicate with a data store, another computing device or server, user terminals, and/or other devices via the network 1408. The user device 1406 may also include I/O device(s) 1430, such as a keyboard, a mouse, a pen, a voice input device, a touch screen input device, a display, speakers, and a printer.

Turning to the contents of the memory 1414 in more detail, the memory 1414 may include an operating system 1413 and/or one or more application programs or services for implementing the features disclosed herein such as applications 1411 (e.g., health application 222, digital wallet, third-party applications, browser application). In some examples, the applications 1411 may include a health application (e.g., the health application 222) to perform similar techniques as described with reference to the user device 1406. Similarly, at least some techniques described with reference to the service provider computer 1402 may be performed by the user device 1406.

The service provider computer 1402 may also be any type of computing device such as, but not limited to, a collection of virtual or "cloud" computing resources, a remote server, a mobile phone, a smartphone, a PDA, a laptop computer, a desktop computer, a thin-client device, a tablet computer, a wearable device, a server computer, or a virtual machine instance. In some examples, the service provider computer 1402 may be in communication with the user device 1406 via the network 1408, or via other network connections.

In one illustrative configuration, the service provider computer 1402 may include at least one memory 1442 and one or more processing units (or processor(s)) 1444. The processor(s) 1444 may be implemented as appropriate in hardware, computer-executable instructions, firmware, or combinations thereof. Computer-executable instruction or firmware implementations of the processor(s) 1444 may include computer-executable or machine-executable instructions written in any suitable programming language to perform the various functions described.

The memory 1442 may store program instructions that are loadable and executable on the processor(s) 1444, as well as data generated during the execution of these programs. Depending on the configuration and type of service provider computer 1402, the memory 1442 may be volatile (such as RAM) and/or non-volatile (such as ROM and flash memory). The service provider computer 1402 may also include additional removable storage and/or non-removable storage 1446 including, but not limited to, magnetic storage, optical disks, and/or tape storage. The disk drives and their associated non-transitory computer-readable media may provide non-volatile storage of computer-readable instructions, data structures, program modules, and other data for the computing devices. In some implementations, the memory 1442 may include multiple different types of memory, such as SRAM, DRAM, or ROM. While the volatile memory described herein may be referred to as RAM, any volatile memory that would not maintain data stored therein, once unplugged from a host and/or power, would be appropriate. The memory 1442 and the additional storage 1446, both removable and non-removable, are both additional examples of non-transitory computer-readable storage media.

The service provider computer 1402 may also contain communications connection(s) 1448 that allow the service provider computer 1402 to communicate with a data store, another computing device or server, user terminals, and/or other devices via the network 1408. The service provider computer 1402 may also include I/O device(s) 1450, such as a keyboard, a mouse, a pen, a voice input device, a touch input device, a display, speakers, and a printer.

Turning to the contents of the memory 1442 in more detail, the memory 1442 may include an operating system 1452 and/or one or more application programs 1441 or services for implementing the features disclosed herein including a provider service 210, the provider admin 212, the subscription service 220, business registration system 208, the test harness 216, the device authentication service 226, the data storage engine 228, the data retrieval engine

234, the assets engine 236, the EHR authentication service 238, the logging engine 242, the access control 230, log 128, and health data storage 232 database, and/or the dashboard 106.

In the following, further examples are described to facilitate the understanding of the present disclosure.

Example 1. In this example, there is provided a computer-implemented method, including:

storing, by a server system, health data for a plurality of users in accordance with a multi-node data structure, each node of the multi-node data structure being encrypted with a unique encryption key and being identified by a unique data identifier;

receiving, by the server system and from a clinician dashboard associated with a health institution, a first request to access a portion of the health data, the first request including (i) a particular unique data identifier associated with a particular node of the multi-node data structure, and (ii) a user identifier associated with a health care professional of the health institution;

generating, by a server system, a transaction record based at least in part on logged information associated with the first request, the transaction record identifying (i) the particular unique data identifier, (ii) the user identifier associated with the user of the health institution, and (iii) metadata associated with the first request;

responsive to receiving a second request to access transaction data corresponding to the health data, querying, by the server system, a database accessibly by the server system in accordance with a search parameter included in the second request;

generating, by the server system, a data package based at least in part on search results generated by querying the database, the data package including the transaction record; and sending, by the server system, the data package to an external system associated with the second request, the transaction record being configured to enable the external system to identify a patient profile associated the particular unique data identifier and the user identifier associated with the health care professional.

Example 2. In this example, there is provided a method of any of the preceding or subsequent examples, further including storing, by the server system, the transaction record in the database accessible by the server system, the database including other transaction records associated with other requests to access the health data, the transaction record being configured to prevent the server system from identifying the patient profile associated the particular unique data identifier or a health care professional profile associated with the health care professional.

Example 3. In this example, there is provided a method of any of the preceding or subsequent examples, wherein the transaction record being configured to enable the external system to identify the patient profile and the user identifier includes the transaction record being configured for comparison with a different dataset that includes a mapping of patient profiles and unique data identifiers.

Example 4. In this example, there is provided a method of any of the preceding or subsequent examples, wherein the external system includes a computer system of an electronic health record system associated with a health institution.

Example 5. In this example, there is provided a method of any of the preceding or subsequent examples, wherein the particular unique data identifier corresponds to a root node of the multi-node data structure.

Example 6. In this example, there is provided a method of any of the preceding or subsequent examples, wherein the root node is associated the patient profile and is linked to other nodes that store other health data for a patient to which the patient profile belongs.

Example 7. In this example, there is provided a method of any of the preceding or subsequent examples, wherein the root node is assigned to a unique health institution responsible for maintaining health records for a patient to which the patient profile belongs.

Example 8. In this example, there is provided a method of any of the preceding or subsequent examples, wherein the transaction record is stored in plain text.

Example 9. In this example, there is provided a method of any of the preceding or subsequent examples, wherein the transaction record is encrypted.

Example 10. In this example, there is provided a method of any of the preceding or subsequent examples, wherein each unique data identifier includes a hash of data stored at the respective node of the multi-node data structure.

Example 11. In this example, there is provided a method of any of the preceding or subsequent examples, wherein the transaction record includes the particular unique data identifier, the user identifier, a health institution identifier, a timestamp, and an IP address.

Example 12. In this example, there is provided a method of any of the preceding or subsequent examples, wherein receiving the first request includes receiving token information, and wherein generating the transaction record based at least in part on the logged information associated with the first request includes extracting at least the user identifier from the token information.

Example 13. In this example, there is provided a method of any of the preceding or subsequent examples, wherein token information is generated by an electronic health record (EHR) system.

Example 14. In this example, there is provided a method of any of the preceding or subsequent examples, wherein the search parameter identifies a health institution identifier.

Example 15. In this example, there is provided one or more non-transitory computer-readable media including computer-executable instructions that, when executed by one or more processors, cause the one or more processors to perform the method of any one of clauses 1-14.

Example 16. In this example, there is provided a computerized system, comprising:
a memory configured to computer-executable instructions; and
a processor configured to access the memory and execute the computer-executable instructions to perform the method of any one of clauses 1-14.

Example 17. In this example, there is provided a computer-implemented method, including:
receiving a cryptographic key and a unique data identifier from an electronic health record (EHR) system;
sending, to a service provider, a first request for health data associated with a user, the first request including a unique data identifier that identifies an encrypted data node of a multi-node data structure used by the service provider to store the health data;
receiving, from the service provider, node information representative of the encrypted data node;
receiving, from the service provider, access information corresponding to the request and the node information;
generating a transaction record based at least in part on the node information and the accessing information, the transaction record identifying (i) the unique data identifier, (ii) user identifier associated with a user of a health institution who requested the health data, and (iii) metadata associated with the first request;
comparing the transaction record with a mapping including user identifiers and patient identifiers; and
identifying a set of records of a particular patient accessed by the user based at least in part on the comparing.

Example 18. In this example, there is provided a method of any of the preceding or subsequent examples, wherein receiving, from the service provider, the node information includes receiving encrypted health data corresponding to the encrypted data node, the method further including decrypting, using the cryptographic key, the encrypted health data.

Example 19. In this example, there is provided a method of any of the preceding or subsequent examples, further including
prior to sending the first request, sending, to the service provider, token information and the unique data identifier; and
receiving an access token from the service provider, the access token representative of successful authentication of the token information by the service provider.

Example 20. In this example, there is provided a method of any of the preceding or subsequent examples, wherein the token information includes a public key associated with the user identifier associated with the health institution.

Example 21. In this example, there is provided a method of any of the preceding or subsequent examples, wherein the token information includes an OpenID token.

Example 22. In this example, there is provided one or more non-transitory computer-readable media including computer-executable instructions that, when executed by one or more processors, cause the one or more processors to perform the method of any one of clauses 15-21.

Example 23. In this example, there is provided a computerized system, including:
a memory configured to computer-executable instructions; and
a processor configured to access the memory and execute the computer-executable instructions to perform the method of any one of clauses 15-21.

Example 24. In this example, there is provided a computer-implemented method, including:
obtaining health data from at least one of (i) a first sensor of a mobile device, (ii) a second sensor of a wearable device, or (iii) a first electronic health record (EHR) system
generating health data records based at least in part on the obtained health data, the health data records organized and stored on the mobile device according to a multi-node data structure, each node of the multi-node data structure identifiable by a unique data identifier;
generating a first set of cryptographic keys corresponding to one or more nodes of the multi-node data structure at which the health data records are stored;
encrypting log data corresponding to the health data records;
associating the encrypted log data with the health data records;
sending the associated encrypted log data and the health data records to a service provider for storage; and
sending a second set of cryptographic keys to the first EHR system or to a second EHR system, the second set of cryptographic keys configured to decrypt the log data.

Example 25. In this example, there is provided a method of any of the preceding or subsequent examples, wherein generating the health data record includes processing the health data, encrypting the health data, and storing the health data on the mobile user device.

Example 26. In this example, there is provided a method of any of the preceding or subsequent examples, wherein the unique data identifier includes a hash of health data stored at the respective node.

Example 27. In this example, there is provided a method of any of the preceding or subsequent examples, wherein the log data is specific to each node of the multi-node data structure and encrypted using individual cryptographic keys of the second set of cryptographic keys.

Example 28. In this example, there is provided a method of any of the preceding or subsequent examples, wherein the first set of cryptographic keys are configured to decrypt encrypted data stored in the multi-node data structure.

Example 29. In this example, there is provided one or more non-transitory computer-readable media including computer-executable instructions that, when executed by one or more processors, cause the one or more processors to perform the method of any one of clauses 24-28.

Example 30. In this example, there is provided a computerized system, including:

a memory configured to computer-executable instructions; and a processor configured to access the memory and execute the computer-executable instructions to perform the method of any one of clauses 24-28.

Example 31. In this example, there is provided a computer-implemented method, including:

beginning decryption of a set of encrypted log entries corresponding to access events of health data;

determining whether a log entry of the set of encrypted log entries includes a portion including a third ciphertext corresponding to a set of encrypted user identifiers; and in the event log entry includes the third cipertext:

trying a set of first cryptographic keys to decrypt the third ciphertext of the log entry, the set of first cryptographic keys associated with to one or more physicians;

upon successful decryption of the third ciphertext, retrieving a patient identifier previously encrypted as the third ciphertext;

using the patient identifier to retrieve a second cryptographic key associated with a patient; and using the second cryptographic key to decrypt one or more other portions of the log entry.

Example 32. In this example, there is provided a method of any of the preceding or subsequent examples, wherein the health data is stored according to a multi-node data structure and each log entry of the set of encrypted log entries corresponds to access of a node of the multi-node data structure.

Example 33. In this example, there is provided a method of any of the preceding or subsequent examples, further including receiving the set of encrypted log entries from a service provider.

Example 34. In this example, there is provided a method of any of the preceding or subsequent examples, further including outputting a log record that includes a decrypted version of the log entry.

Example 35. In this example, there is provided a method of any of the preceding or subsequent examples, further including, in the event the log entry does not include the third ciphertext, trying a set of second cryptographic keys to decrypt the one or more other portions of the log entry, the set of second cryptographic keys corresponding to nodes of a multi-node data structure used to store the health data.

Example 36. In this example, there is provided one or more non-transitory computer-readable media including computer-executable instructions that, when executed by one or more processors, cause the one or more processors to perform the method of any one of clauses 31-35.

Example 37. In this example, there is provided a computerized system, including:

a memory configured to computer-executable instructions; and a processor configured to access the memory and execute the computer-executable instructions to perform the method of any one of clauses 31-35.

The various examples can be further implemented in a wide variety of operating environments, which in some cases can include one or more user computers, computing devices, or processing devices which can be used to operate any of a number of applications. User or client devices can include any of a number of general purpose personal computers, such as desktop or laptop computers running a standard operating system, as well as cellular, wireless, and handheld devices running mobile software and capable of supporting a number of networking and messaging protocols. Such a system also can include a number of workstations running any of a variety of commercially-available operating systems and other known applications for purposes such as development and database management. These devices also can include other electronic devices, such as dummy terminals, thin-clients, gaming systems, and other devices capable of communicating via a network.

Most examples utilize at least one network that would be familiar to those skilled in the art for supporting communications using any of a variety of commercially-available protocols, such as TCP/IP, OSI, FTP, UPnP, NFS, CIFS, and AppleTalk. The network can be, for example, a local area network, a wide-area network, a virtual private network, the Internet, an intranet, an extranet, a public switched telephone network, an infrared network, a wireless network, and any combination thereof.

In examples utilizing a network server, the network server can run any of a variety of server or mid-tier applications, including HTTP servers, FTP servers, CGI servers, data servers, Java servers, and business application servers. The server(s) may also be capable of executing programs or scripts in response to requests from user devices, such as by executing one or more applications that may be implemented as one or more scripts or programs written in any programming language, such as Java®, C, C# or C++, or any scripting language, such as Perl, Python, or TCL, as well as combinations thereof. The server(s) may also include database servers, including without limitation those commercially available from Oracle®, Microsoft®, Sybase®, and IBM®.

The environment can include a variety of data stores and other memory and storage media as discussed above. These can reside in a variety of locations, such as on a storage medium local to (and/or resident in) one or more of the computers or remote from any or all of the computers across the network. In a particular set of examples, the information may reside in a storage-area network (SAN) familiar to those skilled in the art. Similarly, any necessary files for performing the functions attributed to the computers, servers, or other network devices may be stored locally and/or remotely, as appropriate. Where a system includes computerized devices, each such device can include hardware elements that may be electrically coupled via a bus, the elements including, for example, at least one central processing unit (CPU), at least one input device (e.g., a mouse, keyboard, controller, touch screen, keypad), and at least one output device (e.g., a display device, printer, speaker). Such a system may also include one or more storage devices, such as disk drives, optical storage devices, and solid-state storage devices such as RAM or ROM, as well as removable media devices, memory cards, flash cards, etc.

Such devices can also include a computer-readable storage media reader, a communications device (e.g., a modem, a network card (wireless or wired), an infrared communication device), and working memory as described above. The computer-readable storage media reader can be connected with, or configured to receive, a non-transitory computer-readable storage medium, representing remote, local, fixed, and/or removable storage devices as well as storage media for temporarily and/or more permanently containing, storing, transmitting, and retrieving computer-readable information. The system and various devices also typically will include a number of software applications, modules, services, or other elements located within at least one working memory device, including an operating system and application programs, such as a client application or browser. It should be appreciated that alternate examples may have numerous variations from that described above. For example, customized hardware might also be used and/or particular elements might be implemented in hardware, software (including portable software, such as applets), or both. Further, connection to other computing devices such as network input/output devices may be employed.

Non-transitory storage media and computer-readable media for containing code, or portions of code, can include any appropriate media known or used in the art, including storage media, such as, but not limited to, volatile and non-volatile, removable and non-removable media implemented in any method or technology for storage of information such as computer-readable instructions, data structures, program modules, or other data, including RAM, ROM, EEPROM, flash memory or other memory technology, CD-ROM, DVD or other optical storage, magnetic cassettes, magnetic tape, magnetic disk storage or other magnetic storage devices, or any other medium which can be used to store the desired information and which can be accessed by a system device. Based at least in part on the disclosure and teachings provided herein, a person of ordinary skill in the art will appreciate other ways and/or methods to implement the various examples.

The specification and drawings are, accordingly, to be regarded in an illustrative rather than a restrictive sense. It will, however, be evident that various modifications and changes may be made thereunto without departing from the broader spirit and scope of the disclosure as set forth in the claims.

Other variations are within the spirit of the present disclosure. Thus, while the disclosed techniques are susceptible to various modifications and alternative constructions, certain illustrated examples thereof are shown in the drawings and have been described above in detail. It should be understood, however, that there is no intention to limit the disclosure to the specific form or forms disclosed, but on the contrary, the intention is to cover all modifications, alternative constructions and equivalents falling within the spirit and scope of the disclosure, as defined in the appended claims.

The use of the terms "a" and "an" and "the" and similar referents in the context of describing the disclosed examples (especially in the context of the following claims) are to be construed to cover both the singular and the plural, unless otherwise indicated herein or clearly contradicted by context. The terms "comprising," "having," "including," and "containing" are to be construed as open-ended terms (e.g., meaning "including, but not limited to") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate examples of the disclosure and does not pose a limitation on the scope of the disclosure unless otherwise claimed. No language in the specification should be construed as indicating any non-claimed element as essential to the practice of the disclosure.

Disjunctive language such as the phrase "at least one of X, Y, or Z," unless specifically stated otherwise, is otherwise understood within the context as used in general to present that an item, term, etc., may be either X, Y, or Z, or any combination thereof (e.g., X, Y, and/or Z). Thus, such disjunctive language is not generally intended to, and should not, imply that certain examples require at least one of X, at least one of Y, or at least one of Z to each be present.

Preferred examples of this disclosure are described herein, including the best mode known to the inventors for carrying out the disclosure. Variations of those preferred examples may become apparent to those of ordinary skill in the art upon reading the foregoing description. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

As described above, one aspect of the present technology is the gathering and use of data available from various sources to provide a comprehensive and complete window to a user's personal health record. The present disclosure contemplates that in some instances, this gathered data may include personally identifiable information (PII) data that uniquely identifies or can be used to contact or locate a specific person. Such personal information data can include demographic data, location-based data, telephone numbers, email addresses, Twitter IDs, home addresses, data or records relating to a user's health or level of fitness (e.g., vital sign measurements, medication information, exercise information), date of birth, health record data, or any other identifying or personal or health information.

The present disclosure recognizes that the use of such personal information data, in the present technology, can be used to the benefit of users. For example, the personal information data can be used to provide enhancements to a user's personal health record. Further, other uses for personal information data that benefit the user are also contemplated by the present disclosure. For instance, health and fitness data may be used to provide insights into a user's general wellness, or may be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the U.S., collection of or access to certain health data may be governed by federal and/or state laws, such as the Health Insurance Portability and Accountability Act (HIPAA); whereas health data in other countries may be subject to other regulations and policies and should be handled accordingly. Hence, different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of advertisement delivery services or other services relating to health record management, the present technology can be configured to allow users to select to "opt in" or "opt out" of participation in the collection of personal information data during registration for services or anytime thereafter. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health-related applications, data de-identification can be used to protect a user's privacy. De-identification may be facilitated, when appropriate, by removing specific identifiers (e.g., date of birth), controlling the amount or specificity of data stored (e.g., collecting location data at a city level rather than at an address level), controlling how data is stored (e.g., aggregating data across users), and/or other methods.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data.

What is claimed is:

1. A computer-implemented method, comprising:

receiving, by a server system and from a plurality of electronic health record systems, health data associated with a plurality of health records of a plurality of users, wherein each electronic health record system is associated with a health institution that maintains health records of the plurality of health records on behalf of the plurality of users;

storing, by the server system, the health data for the plurality of users in accordance with a multi-node data structure, each node of the multi-node data structure being encrypted with a unique encryption key and being identified by a unique data identifier;

providing to a clinician dashboard associated with a particular health institution, a particular unique data identifier and a root key that is configured to decrypt a root node of the multi-node data structure identified by the particular unique data identifier;

receiving, by the server system and from the clinician dashboard, a first request to access a portion of the health data, the first request comprising (i) the particular unique data identifier associated with the root node of the multi-node data structure, (ii) a user identifier associated with a health care professional of the particular health institution, and (iii) the root key;

generating, by the server system, a transaction record based at least in part on logged information associated with the first request, the transaction record identifying (i) the particular unique data identifier, (ii) the user identifier associated with the health care professional of the particular health institution, and (iii) metadata associated with the first request;

responsive to receiving a second request to access transaction data corresponding to the first request to access the portion of the health data, querying, by the server system, a database accessible by the server system in accordance with a search parameter included in the second request;

generating, by the server system, a data package based at least in part on search results generated by querying the database, the data package comprising the transaction record; and sending, by the server system, the data package to an external system associated with the second request, the transaction record being configured to enable the external system to identify a patient profile associated with the particular unique data identifier and the user identifier associated with the health care professional, wherein the root node is assigned to a unique health institution responsible for maintaining health records for a patient to which the patient profile belongs.

2. The computer-implemented method of claim 1, further comprising storing, by the server system, the transaction record in the database accessible by the server system, the database comprising other transaction records associated with other requests to access the health data, the transaction record comprising an encrypted version of the particular unique data identifier and an encrypted version of the user identifier that prevents the server system from identifying the patient profile associated with the particular unique data identifier or a health care professional profile associated with the health care professional.

3. The computer-implemented method of claim 2, wherein the transaction record being configured to enable the external system to identify the patient profile and the user identifier comprises the transaction record being configured for comparison with a different dataset that includes a mapping of patient profiles and unique data identifiers.

4. The computer-implemented method of claim 1, wherein the external system comprises a computer system of a particular electronic health record system associated with the particular health institution.

5. The computer-implemented method of claim 1, wherein the root node is associated with the patient profile and is linked to other nodes that store other health data for the patient to which the patient profile belongs.

6. One or more non-transitory computer-readable media comprising computer-executable instructions that, when executed by one or more processors of a server system, cause the server system to perform operations comprising:

receiving, by the system and from a plurality of electronic health record systems, health data associated with a plurality of health records of a plurality of users, wherein each electronic health record system is associated with a health institution that maintains health records of the plurality of health records on behalf of the plurality of users;

storing, by the server system, the health data for the plurality of users in accordance with a multi-node data structure, each node of the multi-node data structure being encrypted with a unique encryption key and being identified by a unique data identifier;

providing to a clinician dashboard associated with a particular health institution, a particular unique data identifier and a root key that is configured to decrypt a root node of the multi-node data structure identified by the particular unique data identifier;

receiving, by the server system and from the clinician dashboard, a first request to access a portion of the health data, the first request comprising (i) the particular unique data identifier associated with the root node of the multi-node data structure, (ii) a user identifier associated with a health care professional of the particular health institution, and (iii) the root key;

generating, by the server system, a transaction record based at least in part on logged information associated with the first request, the transaction record identifying (i) the particular unique data identifier, (ii) the user identifier associated with the health care professional of the particular health institution, and (iii) metadata associated with the first request;

responsive to receiving a second request to access transaction data corresponding to the first request to access the portion of the health data, querying, by the server system, a database accessible by the server system in accordance with a search parameter included in the second request;

generating, by the server system, a data package based at least in part on search results generated by querying the database, the data package comprising the transaction record; and sending, by the server system, the data package to an external system associated with the second request, the transaction record being configured to enable the external system to identify a patient profile associated with the particular unique data identifier and the user identifier associated with the health care professional, wherein the root node is assigned to a unique health institution responsible for maintaining health records for a patient to which the patient profile belongs.

7. The one or more non-transitory computer-readable media of claim 6, wherein the transaction record is stored in plain text.

8. The one or more non-transitory computer-readable media of claim 6, wherein the transaction record is encrypted.

9. The one or more non-transitory computer-readable media of claim 6, wherein each unique data identifier comprises a hash of data stored at the respective node of the multi-node data structure.

10. The one or more non-transitory computer-readable media of claim 6, wherein the transaction record further comprises a health institution identifier, a timestamp, and an IP address.

11. The one or more non-transitory computer-readable media of claim 6, wherein receiving the first request comprises receiving token information, and wherein generating the transaction record based at least in part on the logged information associated with the first request comprises extracting at least the user identifier from the token information.

12. The one or more non-transitory computer-readable media of claim 11, wherein the token information is generated by a particular electronic health record system.

13. The one or more non-transitory computer-readable media of claim 12, wherein the search parameter identifies a health institution identifier.

14. A computerized system, comprising:

a memory configured to computer-executable instructions; and a processor configured to access the memory and execute the computer-executable instructions to at least:

receive, from a plurality of electronic health record systems, health data associated with a plurality of health records of a plurality of users, wherein each electronic health record system is associated with a health institution that maintains health records of the plurality of health records on behalf of the plurality of users;

store the health data for the plurality of users in accordance with a multi-node data structure, each node of the multi-node data structure being encrypted with a unique encryption key and being identified by a unique data identifier;

provide to a clinician dashboard associated with a particular health institution, a particular unique data identifier and a root key that is configured to decrypt a root node of the multi-node data structure identified by the particular unique data identifier;

receive, from the clinician dashboard, a first request to access a portion of the health data, the first request comprising (i) the particular unique data identifier associated with the root node of the multi-node data structure, (ii) a user identifier associated with a health care professional of the particular health institution, and (iii) the root key;

generate a transaction record based at least in part on logged information associated with the first request, the transaction record identifying (i) the particular unique data identifier, (ii) the user identifier associated with the health care professional of the particular health institution, and (iii) metadata associated with the first request;

responsive to receiving a second request to access transaction data corresponding to the first request to access the portion of the health data, query a database accessible by the computerized system in accordance with a search parameter included in the second request;

generate a data package based at least in part on search results generated by querying the database, the data package comprising the transaction record; and send the data package to an external system associated with the second request, the transaction record being configured to enable the external system to identify a patient profile associated the particular unique data identifier and the user identifier associated with the health care professional, wherein the root node is assigned to a unique health institution responsible for maintaining health records for a patient to which the patient profile belongs.

15. The system of claim 14, wherein the transaction record being configured to enable the external system to identify the patient profile and the user identifier comprises the transaction record being configured for comparison with a different dataset that includes a mapping of patient profiles and unique data identifiers.

16. The system of claim 14, wherein the external system comprises a computer system of a particular electronic health record system associated with the particular health institution.

17. The system of claim 14, wherein the root node is associated the patient profile and is linked to other nodes that store other health data for the patient to which the patient profile belongs.

18. The computer-implemented method of claim 1, wherein the first request further comprises authentication information useable by the server system to authenticate the first request.

19. The computer-implemented method of claim 1, wherein storing the health data for the plurality of users in accordance with the multi-node data structure comprises receiving, from individual user devices associated with individual users of the plurality of users, individual multi-node data structures specific to the individual users and that have been generated by the individual user devices.

* * * * *